(12) United States Patent
Koepke et al.

(10) Patent No.: US 10,131,884 B2
(45) Date of Patent: Nov. 20, 2018

(54) RECOMBINANT ACETOGENIC BACTERIUM FOR THE CONVERSION OF METHANE TO PRODUCTS

(71) Applicant: LanzaTech New Zealand Limited, Skokie, IL (US)

(72) Inventors: Michael Koepke, Skokie, IL (US); Peter Dürre, Ulm (DE)

(73) Assignee: LANZATECH NEW ZEALAND LIMITED, Auckland (NZ)

( * ) Notice: Subject to any disclaimer, the term of this patent is extended or adjusted under 35 U.S.C. 154(b) by 0 days.

(21) Appl. No.: 15/051,036

(22) Filed: Feb. 23, 2016

(65) Prior Publication Data

US 2016/0244785 A1   Aug. 25, 2016

Related U.S. Application Data

(60) Provisional application No. 62/119,632, filed on Feb. 23, 2015.

(51) Int. Cl.
| | |
|---|---|
| C12P 7/24 | (2006.01) |
| C12N 9/04 | (2006.01) |
| C12N 15/52 | (2006.01) |
| C12N 9/88 | (2006.01) |
| C12N 9/10 | (2006.01) |
| C12P 7/40 | (2006.01) |
| C12N 9/06 | (2006.01) |
| C12N 9/02 | (2006.01) |
| C12N 1/30 | (2006.01) |
| C12P 7/06 | (2006.01) |

(52) U.S. Cl.
CPC ............ *C12N 9/0044* (2013.01); *C12N 1/30* (2013.01); *C12N 9/0071* (2013.01); *C12N 9/0073* (2013.01); *C12P 7/065* (2013.01); *C12Y 114/18003* (2013.01); *C12Y 107/02001* (2013.01); *C12Y 107/02005* (2013.01); *C12Y 114/13025* (2013.01); *Y02E 50/17* (2013.01); *Y02E 50/343* (2013.01)

(58) Field of Classification Search
CPC .... C12N 9/0028; C12N 9/1007; C12N 15/63; C12P 7/24; C12P 7/04; C12Y 107/02001; C12Y 114/13025
USPC ................ 435/252.3, 254.11, 157; 536/23.2
See application file for complete search history.

(56) References Cited

U.S. PATENT DOCUMENTS

| | | |
|---|---|---|
| 6,340,581 B1 | 1/2002 | Gaddy |
| 8,383,376 B2 | 2/2013 | Simpson et al. |
| 8,697,421 B2 | 4/2014 | Burk et al. |

FOREIGN PATENT DOCUMENTS

| | | |
|---|---|---|
| WO | 2012080421 A1 | 6/2012 |
| WO | 2014062703 A1 | 4/2014 |
| WO | 2014165763 A1 | 10/2014 |
| WO | 2015013295 A1 | 1/2015 |

OTHER PUBLICATIONS

Devos et al., Proteins: Structure, Function and Genetics, 2000, vol. 41: 98-107.*
Whisstocks et al. Quarterly Reviews of Biophysics 2003, vol. 36 (3): 307-340.*
Witkowski et al., Biochemistry 38:11643-11650, 1999.*
Kisselev L., Structure, 2002, vol. 10: 8-9.*
Nitschke et al., Phil Tr ROyl Soc 2013,pp. 1-15.*
Ragsdale et al. biochem, bioact, 2008 , pp. 1873-1898.*
Richardson, Metabolism of 2,4,6-trinitrotoluene by clostridium acetobutylicum: Pathway identification and lab-scale evaluation of contaminated soil bioremediation, MS thesis, Rice University, 1998.
International Search Report for International Patent Application No. PCT/US2016/019208, Korean Intellectual Property Office, dated Jun. 30, 2016.
Abrini, Arch Microbiol, 161: 345-351, 1994.
Bédard, Microbiol Rev, 53: 68-84, 1989.
Ettwig, Appl Environ Microbiol, 75: 3656-3662, 2009.
Ettwig, Nature, 464: 543-548, 2010.
Genthner, Appl Environ Microbiol, 42: 12-19, 1981.
Hu, Environ Microbiol Rep, 1: 377-384, 2009.
Kerby, J Bacteriol, 155: 1208-1218, 1983.
Luesken, Environ Microbiol, 14: 1024-1034, 2012.
Marcellin, Low carbon fuels and commodity chemicals from waste gases—Systematic approach to understand energy metabolism in a model acetogen, Green Chem, 2016.
Raghoebarsing, Nature, 440: 918-921, 2006.
Ragsdale, Biochim Biophys Acta, 1784: 1873-1898, 2008.
Tan, J Basic Microbiol, 53: 1-9, 2013 (later published as Tan, J Basic Microbiol, 54: 996-1004, 2014).
Trotsenko, Adv Appl Microbiol, 63: 183-229, 2008.
Witthoff, Appl Environ Microbiol, 79: 6974-6983, 2013.
Wu, Biochem Soc Trans, 39: 243-248, 2011.
Cui, Anaerobic oxidation of methane: and "active" microbial process, Microbiol Open, 4 (1): 1-11, 2014.

(Continued)

*Primary Examiner* — Robert B Mondesi
*Assistant Examiner* — Mohammad Y Meah
(74) *Attorney, Agent, or Firm* — Andrea Schoen

(57) ABSTRACT

The invention provides a recombinant, acetogenic bacterium that consumes a substrate comprising $CH_4$ and converts at least a portion of the $CH_4$ to a product. In particular, the bacterium of may comprise one or more of exogenous methane monooxygenase (MMO), exogenous nitrite reductase (NIR), and exogenous nitric oxide dismutase (NOD). The invention further provides a method for producing a product comprising providing a substrate comprising $CH_4$ to a culture comprising a recombinant, acetogenic bacterium, whereby the bacterium converts at least a portion of the $CH_4$ to a product.

20 Claims, 3 Drawing Sheets

Specification includes a Sequence Listing.

(56) References Cited

OTHER PUBLICATIONS

Wu, Co-localization of particulate methane monooxygenase and cd1 nitrite reductase in the dentrifying methanotroph Candidatus Methylomirabilis oxyfera, FEMS Microbiol Lett, 334 (1): 49-56, 2012.
Kalyuzhnaya, Metabolic engineering in methanotrophic bacteria, Metabol Eng, 29: 142-152, 2015.
Extended European Search Report, EP 16756228.9, dated Jun. 6, 2018.

* cited by examiner

RECOMBINANT ACETOGENIC BACTERIUM FOR THE CONVERSION OF METHANE TO PRODUCTS

CROSS REFERENCE TO RELATED APPLICATIONS

This application claims the benefit of U.S. Patent Application 62/119,632 filed Feb. 23, 2015, the entirety of which is incorporated herein by reference.

BACKGROUND OF THE INVENTION

Methane ($CH_4$) is the second most prevalent greenhouse gas emitted in the United States, accounting for about 9% of all United States greenhouse gas emissions from human activities in 2012. Methane is emitted by natural sources such as wetlands, as well as human activities such as natural gas systems and agriculture. Additionally, methane is much more efficient at trapping radiation than carbon dioxide ($CO_2$), the most prevalent greenhouse gas emitted in the United States. In fact, pound for pound, the comparative impact of methane on climate change is over 20 times greater than carbon dioxide over a 100-year period (United States Environmental Protection Agency).

Methanotrophs are microorganisms that oxidize methane to carbon dioxide and water via the intermediates methanol, formaldehyde, and formate. They play a major role in reducing the methane released from natural environments such as rice paddies, landfills, bogs, and swamps, where methane production is relatively high. As such, methanotrophs have attracted attention from environmental scientists for their potential in bioremediation efforts, namely the reduction of atmospheric methane levels and the mitigation of the effects of global warming.

Aerobic methanotrophs overcome the high activation energy (439 kJ/mol) (Trotsenko, *Adv Appl Microbiol*, 63: 183-229, 2008) required to break the C—H bond of methane by using oxygen as a highly reactive co-substrate for the initial attack, in a reaction catalysed by methane monooxygenase. In particular, methane monooxygenase uses two reducing equivalents from NAD(P)H to split the O—O bond of $O_2$, whereby one atom is reduced to water and the second atom is incorporated into the substrate to yield methanol: $CH_4 + NAD(P)H + H^+ + O_2 \rightarrow CH_3OH + NAD(P)^+ + H_2O$. However, gaseous substrates comprising methane and oxygen are highly combustible, rendering industrial-scale growth of aerobic methanotrophs problematic, if not prohibitively dangerous.

Prior to the discovery of Candidatus *Methylomirabilis oxyfera* (Ettwig, *Nature*, 464: 543-548, 2010), it was believed that that anaerobic oxidation of methane by a single microorganism was biologically impossible (Wu, *Biochem Soc Trans*, 39: 243-248, 2011). Instead of scavenging oxygen from the environment, like the aerobic methanotrophs, or driving methane oxidation by reverse methanogenesis, like the methanogenic archaea in syntrophic consortia of methanotrophic archaea and reducing bacteria, *M. oxyfera* produces its own supply of oxygen by metabolizing nitrite via nitric oxide into oxygen and dinitrogen gas (Raghoebarsing, *Nature*, 440: 918-921, 2006; Ettwig, *Appl Environ Microbiol*, 75: 3656-3662, 2009; Hu, *Environ Microbiol Rep*, 1: 377-384, 2009; Ettwig, *Nature*, 464: 543-548, 2010; Luesken, *Environ Microbiol*, 14: 1024-1034, 2012). The intracellularly produced oxygen is then used for the oxidation of methane by the classical aerobic methane oxidation pathway involving methane monooxygenase (Ettwig, *Nature*, 464: 543-548, 2010).

Although *M. oxyfera* does not require a combustible gaseous substrate containing methane and oxygen like aerobic methanotrophs, *M. oxyfera* has not yet been isolated in pure culture, grown at scale, or shown to produce any commercially valuable products. Accordingly, there remains a strong need for microorganisms and methods capable of converting methane to useful products, such as alcohols or acids.

SUMMARY OF THE INVENTION

The invention provides a recombinant, acetogenic bacterium that consumes a substrate comprising $CH_4$ and converts at least a portion of the $CH_4$ to a product. The invention further provides a method for producing a product comprising providing a substrate comprising $CH_4$ to a culture comprising a recombinant, acetogenic bacterium, whereby the bacterium converts at least a portion of the $CH_4$ to a product. In particular, the bacterium may comprise one or more of exogenous methane monooxygenase (MMO), exogenous nitrite reductase (NIR), and exogenous nitric oxide dismutase (NOD).

In one embodiment, the methane monooxygenase, nitrite reductase, or nitric oxide dismutase are derived from *Methylomirabilis oxyfera*. The methane monooxygenase may be *Methylomirabilis oxyfera* particulate methane monooxygenase A-subunit (EC: 1.14.13.25) (SEQ ID NO: 1), particulate methane monooxygenase B-subunit (EC: 1.14.13.25) (SEQ ID NO: 3), particulate methane monooxygenase C-subunit (EC: 1.14.13.25) (SEQ ID NO: 5), or particulate methane monooxygenase C-subunit2 (EC: 1.14.13.25) (SEQ ID NO: 7). The methane monooxygenase may be encoded by *Methylomirabilis oxyfera* particulate methane monooxygenase A-subunit (pmoA) (SEQ ID NO: 2), particulate methane monooxygenase B-subunit (pmoB) (SEQ ID NO: 4), particulate methane monooxygenase C-subunit (pmoC) (SEQ ID NO: 6), or particulate methane monooxygenase C-subunit2 (pmoC2) (SEQ ID NO: 8). The nitrite reductase may be *Methylomirabilis oxyfera* nitrite reductase, cytochrome cd1 type (EC: 1.7.2.1) (SEQ ID NO: 9). The nitrite reductase may be encoded by *Methylomirabilis oxyfera* nitrite reductase, cytochrome cd1 type (nirS) (SEQ ID NO: 10). The nitric oxide dismutase may be *Methylomirabilis oxyfera* cytochrome c oxidase subunit I (EC: 1.7.2.5) (SEQ ID NO: 11 or 13). The nitric oxide dismutase may be encoded by *Methylomirabilis oxyfera* cytochrome c oxidase subunit I (norZ) (SEQ ID NO: 12 or 14).

In one embodiment, the bacterium of the invention further comprises exogenous methanol methyltransferase. The methanol methyltransferase may be derived from *Acetoanaerobium romashkovii*, *Acetobacterium carbolinicum*, *Acetobacterium dehalogenans*, *Acetobacterium psammolithicum*, *Acetobacterium tundrae*, *Acetobacterium woodii*, *Butyribacterium methylotrophicum*, *Clostridium clariflavum*, *Clostridium formicoaceticum*, *Clostridium magnum*, *Clostridium ethoxybenzovorans*, *Desulfosporosinus meridiei*, *Eubacterium aggregans*, *Eubacterium limosum*, *Moorella mulderi*, *Moorella thermoacetica*, *Moorella thermoautotrophica*, *Sporomusa acidovorans*, *Sporomusa aerivorans*, *Sporomusa malonica*, *Sporomusa paucivorans*, *Sporomusa silvacetica*, *Sporomusa termitida*, or *Thermoacetogenium phaeum*. The methanol methyltransferase may be *Moorella thermoacetica* methanol: corrinoid methyltransferase (EC: 2.1.1.90) (SEQ ID NO: 15), *Moorella thermoacetica* methanol:corrinoid methyltransferase (EC: 2.1.1.246) (SEQ ID NO: 17 or 19), *Acetobacterium woodii* methanol:corrinoid methyltransferase (EC: 2.1.1.90) (SEQ ID NO: 21), *Eubacterium limosum* methanol:corrinoid methyltransferase (EC: 2.1.1.90) (SEQ ID NO: 23), or *Thermoacetogenium phaeum* methanol:corrinoid methyltransferase (EC: 2.1.1.90) (SEQ ID NO: 25). The methanol methyltransferase may be encoded by *Moorella thermoacetica* methanol:corrinoid methyltransferase (mtaB) (SEQ ID NO: 16), *Moorella thermoacetica* methanol:corrinoid methyltransferase (mtaA) (SEQ ID NO: 18 or 20), *Acetobacterium woodii* methanol:corrinoid methyltransferase (mttB18) (SEQ ID NO: 22), *Eubacterium limosum* methanol:corrinoid methyltransferase (mtaB) (SEQ ID NO: 24), or *Thermoacetogenium phaeum* methanol:corrinoid methyltransferase (mtaB) (SEQ ID NO: 26).

In one embodiment, the bacterium of the invention is a member of genus *Clostridium* or *Acetobacterium*. For example, the bacterium of the invention may be derived from *Clostridium autoethanogenum, Clostridium ljungdahlii, Clostridium ragsdalei,* or *Acetobacterium woodii*. In a preferred embodiment, the bacterium of the invention is derived from *Clostridium autoethanogenum* deposited under DSMZ accession number DSM23693.

In addition to $CH_4$, the substrate may further comprise one or more of CO, $CO_2$, and $H_2$. In one embodiment, the substrate may further comprise one or more of $NO_2^-$ and $NO_3^-$. In another embodiment, $CH_4$ is the sole carbon source for the bacterium of the invention. The $CH_4$ may be sourced, for example, from natural gas, agriculture, landfills, wastewater, or biogas production plants.

The bacterium of the invention typically produces one or more products, such as ethanol, acetate, butanol, butyrate, 2,3-butanediol, lactate, butene, butadiene, methyl ethyl ketone (2-butanone), ethylene, acetone, isopropanol, lipids, 3-hydroxypropionate (3-HP), isoprene, fatty acids, 2-butanol, 1,2-propanediol, and 1-propanol.

DETAILED DESCRIPTION OF THE INVENTION

Figure 1:
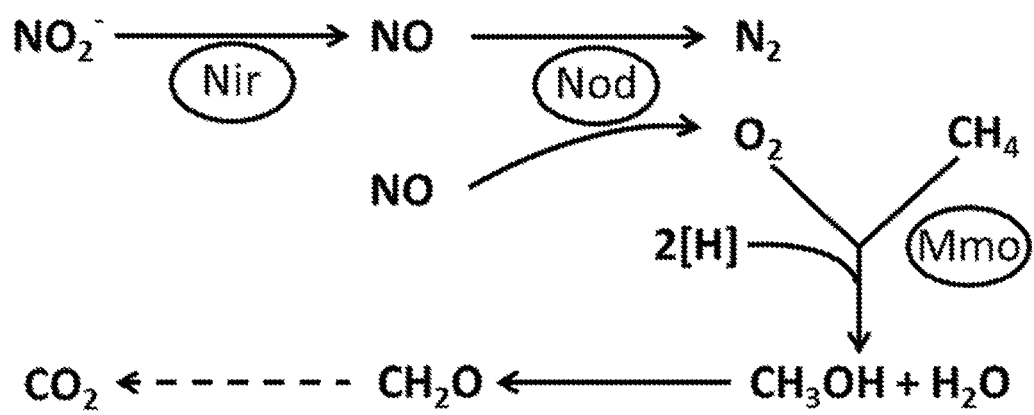
FIG. 1 is a diagram showing the reactions catalyzed by MMO, NIR, and NOD.
Figure 2:
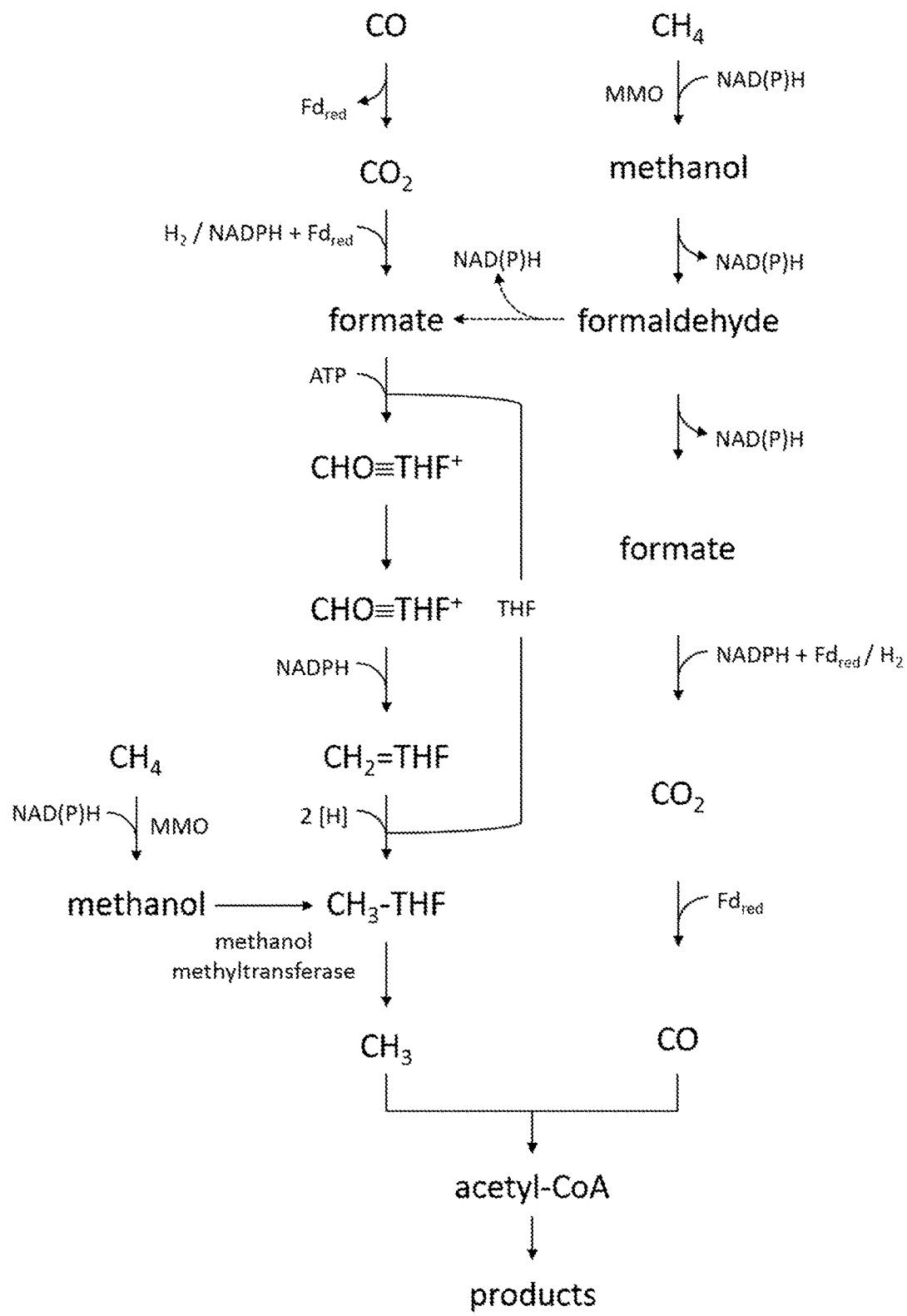
FIG. 2 is a diagram showing the incorporation of a methane utilization module into the Wood-Ljungdahl pathway of acetogens.

An "acetogen" is a microorganism that generates or is capable of generating acetate as a product of anaerobic respiration. Typically, acetogens are obligate anaerobic bacteria that use the Wood-Ljungdahl pathway as their main mechanism for energy conservation and for synthesis of acetyl-CoA and acetyl-CoA-derived products, such as acetate (Ragsdale, *Biochim Biophys Acta,* 1784: 1873-1898, 2008). Acetogens can use a wide variety of carbon sources, including carbon dioxide, carbon monoxide, formate, methanol, methyl groups from methoxylated aromatic compounds, sugars, glyoxylate, glycolate, oxalate, lactate, pyruvate, and short-chain fatty acids (Ragsdale, *Biochim Biophys Acta,* 1784: 1873-1898, 2008). However, acetogens have never been shown to use $CH_4$ as a carbon source.

The invention provides a recombinant, acetogenic bacterium that consumes a substrate comprising $CH_4$ and converts at least a portion of the $CH_4$ to a product. Additionally, the invention provides a method for producing a product comprising providing a substrate comprising $CH_4$ to a culture comprising a recombinant, acetogenic bacterium, whereby the bacterium converts the $CH_4$ to a product.

In particular, the bacterium of the invention may comprise one or more of methane monooxygenase (MMO), nitrite reductase (NIR), and nitric oxide dismutase (NOD). Specifically, the bacterium of the invention may comprise one or more of exogenous MMO, exogenous NIR, and exogenous NOD. In one embodiment, the bacterium of the invention comprises exogenous MMO, but not exogenous NIR or exogenous NOD. In another embodiment, the bacterium of the invention comprises each of exogenous MMO, exogenous NIR, and exogenous NOD. The MMO, NIR, and NOD, or the genes encoding the MMO, NIR, and NOD, may be derived from any suitable microorganism. Preferably, the MMO, NIR, and NOD, or the genes encoding the MMO, NIR, and NOD, are derived from *M. oxyfera*.

Methane monooxygenase (MMO) belongs to the class of oxidoreductase enzymes and oxidizes the C—H bond in methane and other alkanes (EC: 1.14.13.25). In particular, MMO uses two reducing equivalents from NAD(P)H to split the O—O bond of $O_2$, whereby one atom is reduced to water by a 2 e⁻ reduction and the second atom is incorporated into the substrate to yield methanol: $CH_4+O_2+NAD(P)H+H^+ \rightarrow CH_3OH+NAD(P)^++H_2O$. Furthermore, MMO has been described to oxidize CO to $CO_2$ (Bédard, *Microbiol Rev,* 53: 68-84, 1989). While methanotrophs are unable to utilize $CO_2$, many acetogens, including carboxydotrophic acetogens such as *C. autoethanogenum*, are able to utilize $CO_2$. Accordingly, expression of MMO in an acetogen would allow for not only methane utilization, but also increased CO oxidation and increased $CO_2$ utilization. The MMO may be or may be derived from *M. oxyfera* particulate methane monooxygenase A-subunit (EC: 1.14.13.25) (KEGG DAMO_2450) (SEQ ID NO: 1), particulate methane monooxygenase B-subunit (EC: 1.14.13.25) (KEGG DAMO_2448) (SEQ ID NO: 3), particulate methane monooxygenase C-subunit (EC: 1.14.13.25) (KEGG DAMO_2451) (SEQ ID NO: 5), or particulate methane monooxygenase C-subunit2 (EC: 1.14.13.25) (KEGG DAMO_2339) (SEQ ID NO: 7). Additionally, the MMO may be encoded by a gene comprising or derived from *M. oxyfera* particulate methane monooxygenase A-subunit (pmoA) (KEGG DAMO_2450) (SEQ ID NO: 2), particulate methane monooxygenase B-subunit (pmoB) (KEGG DAMO_2448) (SEQ ID NO: 4), particulate methane monooxygenase C-subunit (pmoC) (KEGG DAMO_2451) (SEQ ID NO: 6), or particulate methane monooxygenase C-subunit2 (pmoC2) (KEGG DAMO_2339) (SEQ ID NO: 8).

Nitrite reductase (NIR) catalyses the reduction of nitrite ($NO_2^-$) to nitric oxide (NO) (EC: 1.7.2.1). The NIR may be or may be derived from *M. oxyfera* nitrite reductase, cytochrome cd1 type (nirS) (EC: 1.7.2.1) (KEGG DAMO_2415) (SEQ ID NO: 9). Additionally, the NIR may be encoded by a gene comprising or derived from *M. oxyfera* nitrite reductase, cytochrome cd1 type (nirS) (KEGG DAMO_2415) (SEQ ID NO: 10). In certain embodiments, NIR is present natively (endogenously), such as in *Clostridium autoethanogenum* (YP_008699106). However, even in embodiments where NIR is present natively, it may be necessary to introduce an additional exogenous NIR that is better able to form a complex with and/or interact with MMO.

Nitric oxide dismutase (NOD) catalyses the reaction of two molecules of NO into $N_2$ and $O_2$. The $O_2$ can then be immediately used in the MMO reaction. The NOD may be or may be derived from *M. oxyfera* cytochrome c oxidase subunit I (EC: 1.7.2.5) (KEGG DAMO_2434 or DAMO_2437) (SEQ ID NO: 11 or 13). Additionally, the NOD may be encoded by a gene comprising or derived from *M. oxyfera* cytochrome c oxidase subunit I (norZ) (KEGG DAMO_2434 or DAMO_2437) (SEQ ID NO: 12 or 14). In certain embodiments, NOD is present natively (endogenously), such as in *Clostridium autoethanogenum* (YP008698458). However, even in embodiments where NOD is present natively, it may be necessary to introduce an additional exogenous NOD that is better able to form a complex with and/or interact with MMO.

In certain embodiments, the bacterium of the invention further comprises exogenous methanol methyltransferase. Methanol methyltransferase is responsible for conversion of methanol into the methyl-group of methylenetetrahydrofolate which can then be transferred to the methyl group of acetyl-CoA catalyzed by methyltransferase, corrinoid protein, and CO dehydrogenase/acetyl CoA synthase enzymes of the Wood-Ljungdahl pathway of acetogenic microorganisms. In some microorganisms, a methanol methyltransferase is present natively (endogenously), such as in *Aetoanaerobium romashkovii*, *Acetobacterium carbolinicum*, *Acetobacterium dehalogenans*, *Acetobacterium psammolithicum*, *Acetobacterium tundrae*, *Acetobacterium woodii*, *Butyribacterium methylotrophicum*, *Clostridium clariflavum*, *Clostridium formicoaceticum*, *Clostridium magnum*, *Clostridium ethoxybenzovorans*, *Desulfosporosinus meridiei*, *Eubacterium aggregans*, *Eubacterium limosum*, *Moorella mulderi*, *Moorella thermoacetica*, *Moorella thermoautotrophica*, *Sporomusa acidovorans*, *Sporomusa aerivorans*, *Sporomusa malonica*, *Sporomusa paucivorans*, *Sporomusa silvacetica*, *Sporomusa termitida*, and *Thermoacetogenium phaeum*. In these embodiments, it is not required for the bacterium of the invention to comprise exogenous methanol methyltransferase. However, other microorganisms, such as *Clostridium autoethanogenum*, do not have a native methanol methyltransferase. In these microorganisms, it may be necessary to provide the bacterium of the invention with an exogenous methanol methyltransferase. While the Wood-Ljungdahl pathway is ATP negative (i.e., requires ATP for formate activation), methanol methyltransferase allows the energy-requiring step of the Wood-Ljungdahl pathway to be circumvented, providing the microorganism with additional energy for product synthesis.

The methanol methyltransferase may be derived from any suitable microorganism. In particular, the methanol methyltransferase may be derived from *Acetoanaerobium romashkovii*, *Acetobacterium carbolinicum*, *Acetobacterium dehalogenans*, *Acetobacterium psammolithicum*, *Acetobacterium tundrae*, *Acetobacterium woodii*, *Butyribacterium methylotrophicum*, *Clostridium clariflavum*, *Clostridium formicoaceticum*, *Clostridium magnum*, *Clostridium ethoxybenzovorans*, *Desulfosporosinus meridiei*, *Eubacterium aggregans*, *Eubacterium limosum*, *Moorella mulderi*, *Moorella thermoacetica*, *Moorella thermoautotrophica*, *Sporomusa acidovorans*, *Sporomusa aerivorans*, *Sporomusa malonica*, *Sporomusa paucivorans*, *Sporomusa silvacetica*, *Sporomusa termitida*, or *Thermoacetogenium phaeum*.

In one embodiment, the methanol methyltransferase, or the gene encoding the methanol methyltransferase, is derived from *Moorella thermoacetica*. The methanol methyltransferase may be or may be derived from *Moorella thermoacetica* methanol:corrinoid methyltransferase (EC: 2.1.1.90) (KEGG Moth_1209) (SEQ ID NO: 15) or methanol:corrinoid methyltransferase (EC: 2.1.1.246) (KEGG Moth_2346 or Moth_2100) (SEQ ID NO: 17 or 19). Additionally, the methanol methyltransferase may be encoded by a gene comprising or derived from *Moorella thermoacetica* methanol:corrinoid methyltransferase (mtaB) (KEGG Moth_1209) (SEQ ID NO: 16) or methanol:corrinoid methyltransferase (mtaA) (KEGG Moth_2346 or Moth_2100) (SEQ ID NO: 18 or 20).

In one embodiment, the methanol methyltransferase, or the gene encoding the methanol methyltransferase, is derived from *Acetobacterium woodii* (Kerby, *J Bacteriol*, 155: 1208-1218, 1983), *Eubacterium limosum* (Genthner, *Appl Environ Microbiol*, 42: 12-19, 1981), or *Thermoacetogenium phaeum*. The methanol methyltransferase may be or may be derived from *Acetobacterium woodii* methanol:corrinoid methyltransferase (EC: 2.1.1.90) (KEGG Awo_c22760) (SEQ ID NO: 21), *Eubacterium limosum* methanol:corrinoid methyltransferase (EC: 2.1.1.90) (KEGG ELI_2003) (SEQ ID NO: 23), or *Thermoacetogenium phaeum* methanol:corrinoid methyltransferase (EC: 2.1.1.90) (KEGG Tph_c03590) (SEQ ID NO: 26). Additionally, the methanol methyltransferase may be encoded by a gene comprising or derived from *Acetobacterium woodii* methanol:corrinoid methyltransferase (mttB18) (KEGG Awo_c22760) (SEQ ID NO: 22), *Eubacterium limosum* methanol:corrinoid methyltransferase (mtaB) (KEGG ELI_2003) (SEQ ID NO: 24), or *Thermoacetogenium phaeum* methanol:corrinoid methyltransferase (mtaB) (KEGG Tph_c03590) (SEQ ID NO: 26).

Figure 3:
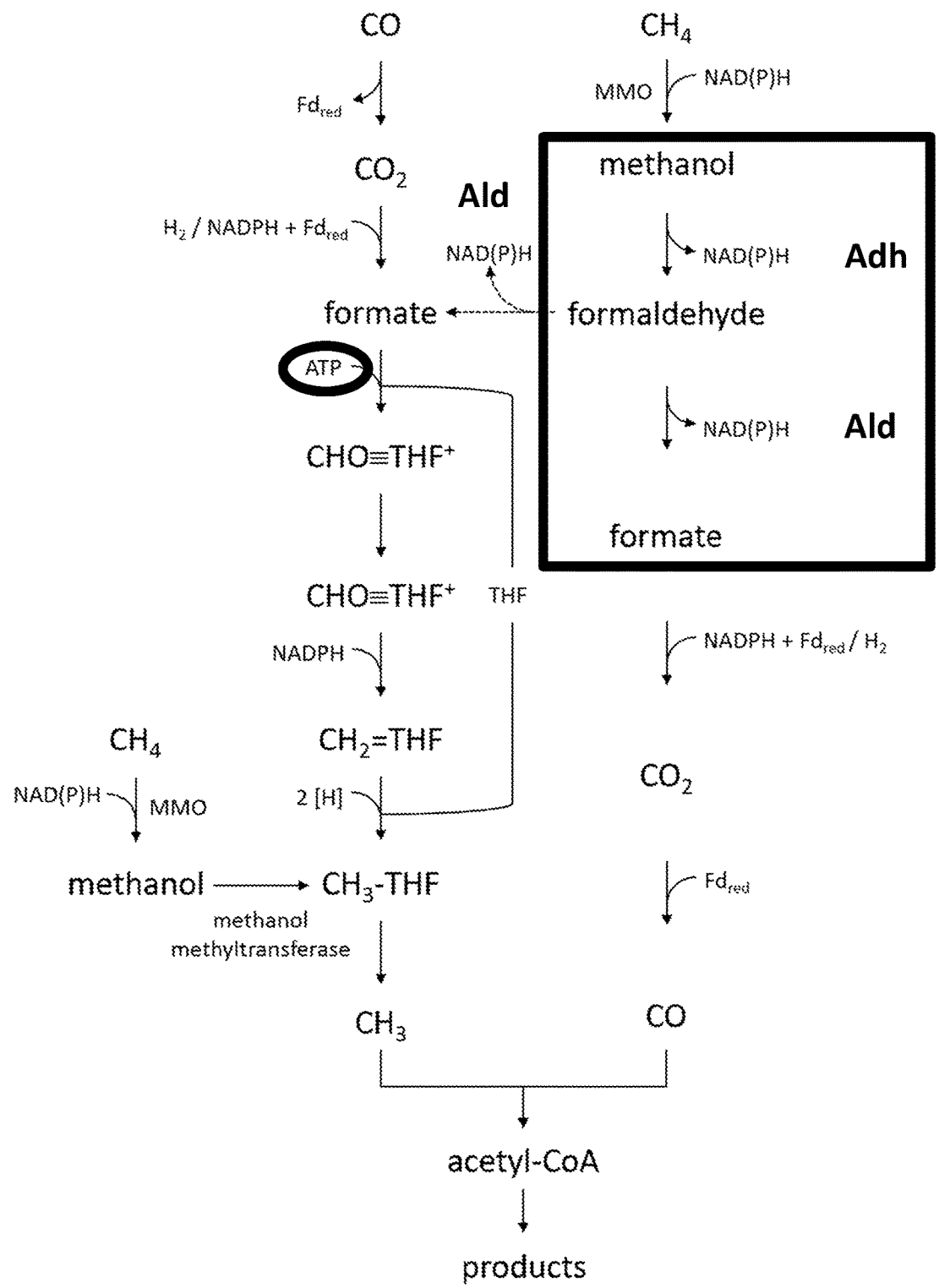
FIG. 3 is a diagram showing methane to formate conversion using an alcohol dehydrogenase (Adh) and an aldehyde dehydrogenase (Ald).

In certain embodiments, the bacterium of the invention further comprises one or both of exogenous alcohol dehydrogenase (Adh) and exogenous aldehyde dehydrogenase (Ald), which enzymes may be required for conversion of methanol to formate (FIG. 3) (Witthoff, *Appl Environ Microbiol*, 79: 6974-6983, 2013). In some embodiments, the bacterium of the invention may natively comprise Adh or Ald, such that exogenous Adh or Ald may not be required. For example, *Clostridium ljungdahlii* natively comprises two Adh enzymes capable of converting methanol to formate (Tan, *J Basic Microbiol*, 54: 996-1004, 2014). Homologues of these enzymes are present in *Clostridium autoethanogenum* (KEGG CAETHG_0555 and CAETHG_1841). However, even in bacteria that natively comprise one or both of Adh and Ald, incorporation of exogenous Adh or Ald into the bacterium of the invention may enhance the conversion of formate to methanol.

"Endogenous" refers to a nucleic acid or protein that is present or expressed in the wild-type or parental bacterium from which the recombinant bacterium of the invention is derived. For example, an endogenous gene is a gene that is natively present in the wild-type or parental bacterium from which the recombinant bacterium of the invention is derived. In one embodiment, the expression of an endogenous gene may be controlled by an exogenous regulatory element, such as an exogenous promoter.

"Exogenous" refers to a nucleic acid or protein that is not present in the wild-type or parental microorganism from which the bacterium of the invention is derived. In one embodiment, an exogenous gene or enzyme may be derived from a heterologous strain or species and introduced to or expressed in the bacterium of the invention. In another embodiment, an exogenous gene or enzyme may be artificially or recombinantly created and introduced to or expressed in the bacterium of the invention. Exogenous nucleic acids may be adapted to integrate into the genome of the bacterium of the invention or to remain in an extra-chromosomal state in the bacterium of the invention, for example, in a plasmid.

"Enzyme activity" refers broadly to enzymatic activity, including, but not limited, to the activity of an enzyme, the amount of an enzyme, or the availability of an enzyme to catalyze a reaction. Accordingly, "increasing" enzyme activity includes increasing the activity of an enzyme, increasing the amount of an enzyme, or increasing the availability of an enzyme to catalyze a reaction.

"Mutated" refers to a nucleic acid or protein that has been modified in the bacterium of the invention compared to the wild-type or parental microorganism from which the bacterium of the invention is derived. In one embodiment, the mutation may be a deletion, insertion, or substitution in a gene encoding an enzyme. In another embodiment, the mutation may be a deletion, insertion, or substitution of one or more amino acids in an enzyme.

"Codon optimization" refers to the mutation of a nucleic acid, such as a gene, for optimized or improved translation of the nucleic acid in a particular strain or species. Codon optimization may result in faster translation rates or higher translation accuracy. In a preferred embodiment, the genes of the invention are codon optimized for expression in *Clostridium*, particularly *Clostridium autoethanogenum, Clostridium ljungdahlii*, or *Clostridium ragsdalei*. In a further preferred embodiment, the genes of the invention are codon optimized for expression in *Clostridium autoethanogenum* LZ1561, which is deposited under DSMZ accession number DSM23693.

"Overexpressed" refers to an increase in expression of a nucleic acid or protein in the bacterium of the invention compared to the wild-type or parental bacterium from which the bacterium of the invention is derived. Overexpression may be achieved by any means known in the art, including modifying gene copy number, gene transcription rate, gene translation rate, or enzyme degradation rate.

The term "genetic modification" broadly refers to manipulation of the genome or nucleic acids of a microorganism. Methods of genetic modification include heterologous gene expression, gene or promoter insertion or deletion, altered gene expression or inactivation, enzyme engineering, directed evolution, knowledge-based design, random mutagenesis methods, gene shuffling, and codon optimization. Such methods are described, for example, in Sambrook, Molecular Cloning: A Laboratory Manual, Cold Spring Harbor Laboratory Press, Cold Spring Harbor, N.Y., 2001; Pleiss, *Curr Opin Biotechnol*, 22: 611-617, 2011; Park, Protein Engineering and Design, CRC Press, 2010.

The term "variants" includes nucleic acids and proteins whose sequence varies from the sequence of a reference nucleic acid and protein, such as a sequence of a reference nucleic acid and protein disclosed in the prior art or exemplified herein. The invention may be practiced using variant nucleic acids or proteins that perform substantially the same function as the reference nucleic acid or protein. For example, a variant protein may perform substantially the same function or catalyze substantially the same reaction as a reference protein. A variant gene may encode the same or substantially the same protein as a reference gene. A variant promoter may have substantially the same ability to promote the expression of one or more genes as a reference promoter.

Such nucleic acids or proteins may be referred to herein as "functionally equivalent variants." By way of example, functionally equivalent variants of a nucleic acid may include allelic variants, fragments of a gene, mutated genes, polymorphisms, and the like. Homologous genes from other microorganisms are also examples of functionally equivalent variants. These include homologous genes in species such as *Clostridium acetobutylicum, Clostridium beijerinckii*, or *Clostridium ljungdahlii*, the details of which are publicly available on websites such as Genbank or NCBI. Functionally equivalent variants also includes nucleic acids whose sequence varies as a result of codon optimization for a particular organism. A functionally equivalent variant of a nucleic acid will preferably have at least approximately 70%, approximately 80%, approximately 85%, approximately 90%, approximately 95%, approximately 98%, or greater nucleic acid sequence identity (percent homology) with the referenced nucleic acid. A functionally equivalent variant of a protein will preferably have at least approximately 70%, approximately 80%, approximately 85%, approximately 90%, approximately 95%, approximately 98%, or greater amino acid identity (percent homology) with the referenced protein. The functional equivalence of a variant nucleic acid or protein may be evaluated using any method known in the art.

Nucleic acids may be delivered to a bacterium of the invention using any method known in the art. For example, nucleic acids may be delivered as naked nucleic acids or may be formulated with one or more agents (e.g., liposomes). The nucleic acids may be DNA, RNA, cDNA, or combinations thereof, as is appropriate. Restriction inhibitors may be used in certain embodiments (Murray, *Microbiol Molec Biol Rev*, 64: 412-434, 2000). Additional vectors may include plasmids, viruses (including bacteriophage), cosmids, and artificial chromosomes. In a preferred embodiment, nucleic acids are delivered to the bacterium of the invention using a plasmid.

By way of example, transformation (including transduction or transfection) may be achieved by electroporation, ultrasonication, polyethylene glycol-mediated transformation, chemical or natural competence, protoplast transformation, prophage induction, or conjugation (see, e.g., Molecular Cloning: A Laboratory Manual, Cold Spring Harbor Laboratory Press, Cold Spring Harbor, N.Y., 1989). The use of electroporation has been reported for several carboxydotrophic acetogens, including *Clostridium ljungdahlii* (Köpke, *PNAS*, 107:13087-13092, 2010; WO/2012/053905), *Clostridium autoethanogenum* (WO/2012/053905), *Clostridium aceticum* (Schiel-Bengelsdorf, *Synthetic Biol*, 15: 2191-2198, 2012), and *Acetobacterium woodii* (Strätz, *Appl Environ Microbiol*, 60: 1033-1037, 1994). The use of electroporation has also been reported in Clostridia, including *Clostridium acetobutylicum* (Mermelstein, *Biotechnol*, 10: 190-195, 1992), and *Clostridium cellulolyticum* (Jennert, *Microbiol*, 146: 3071-3080, 2000). Prophage induction has been demonstrated for carboxydotrophic acetogens, including *Clostridium scatologenes* (Parthasarathy, Development of a Genetic Modification System in *Clostridium scatologenes* ATCC 25775 for Generation of Mutants, Masters Project, Western Kentucky University, 2010), and conjugation been described for many Clostridia, including *Clostridium difficile* (Herbert, *FEMS Microbiol Lett*, 229: 103-110, 2003) and *Clostridium acetobuylicum* (Williams, *J Gen Microbiol*, 136: 819-826, 1990). In certain embodiments having active restriction enzyme systems, it may be necessary to methylate a nucleic acid before introduction of the nucleic acid into the bacterium of the invention.

A "microorganism" is a microscopic organism, especially a bacterium, archea, virus, or fungus. The microorganism of the invention is typically a bacterium. As used herein, recitation of "microorganism" should be taken to encompass "bacterium."

The term "recombinant" indicates that a nucleic acid, protein, or microorganism is the product of genetic modification or recombination. Generally, the term "recombinant" refers to a nucleic acid, protein, or microorganism that contains or is encoded by genetic material derived from multiple sources, such as two or more different strains or species of microorganisms. As used herein, the term "recombinant" may also be used to describe a microorganism that comprises a mutated nucleic acid or protein, including a mutated form of an endogenous nucleic acid or protein.

A "parental microorganism" is a microorganism used to generate a bacterium of the invention. The parental microorganism may be a naturally-occurring microorganism (i.e., a wild-type microorganism) or a microorganism that has been previously modified (i.e., a mutant or recombinant microorganism). The bacterium of the invention may be modified to express or overexpress one or more enzymes that were not expressed or overexpressed in the parental microorganism. Similarly, the bacterium of the invention may be modified to contain one or more genes that were not contained by the parental microorganism. In one embodiment, the parental organism is *Clostridium autoethanogenum*, *Clostridium ljungdahlii*, or *Clostridium ragsdalei*. In a preferred embodiment, the parental microorganism is *Clostridium autoethanogenum* LZ1561, which was deposited on Jun. 7, 2010 with Deutsche Sammlung von Mikroorganismen and Zellkulturen GmbH (DSMZ) located at Inhoffenstraß 7B, D-38124 Braunschwieg, Germany on Jun. 7, 2010 under the terms of the Budapest Treaty and accorded accession number DSM23693.

The term "derived from" indicates that a nucleic acid, protein, or microorganism is modified or adapted from a different (e.g., a parental or wild-type) nucleic acid, protein, or microorganism, so as to produce a new nucleic acid, protein, or microorganism. Such modifications or adaptations typically include insertion, deletion, mutation, or substitution of nucleic acids or genes. Generally, the bacterium of the invention is derived from a parental microorganism. In one embodiment, the bacterium of the invention is derived from *Clostridium autoethanogenum*, *Clostridium ljungdahlii*, or *Clostridium ragsdalei*. In a preferred embodiment, the bacterium of the invention is derived from *Clostridium autoethanogenum* LZ1561, which is deposited under DSMZ accession DSM23693.

An "acetogen" is a microorganism that generates or is capable of generating acetate as a product of anaerobic respiration. Typically, acetogens are obligately anaerobic bacteria that use the Wood-Ljungdahl pathway as their main mechanism for energy conservation and for synthesis of acetyl-CoA and acetyl-CoA-derived products, such as acetate (Ragsdale, *Biochim Biophys Acta*, 1784: 1873-1898, 2008). Typically, the bacterium of the invention is an acetogen. The bacterium of the invention may be selected or derived from the genus *Clostridium, Morella, Carboxydothermus, Acetogenium, Acetobacterium, Acetoanaerobium, Butyribaceterium,* or *Peptostreptococcus*. In a preferred embodiment, the bacterium of the invention is a member of genus *Clostridium*. In a more preferred embodiment, the bacterium of the invention is derived from *Clostridium autoethanogenum, Clostridium ljungdahlii, Clostridium ragsdalei,* or *Acetobacterium woodii*. In an even more preferred embodiment, the bacterium of the invention is derived from *Clostridium autoethanogenum* deposited under DSMZ accession number DSM23693.

A "carboxydotroph" is a microorganism capable of tolerating a high concentration of carbon monoxide (CO). In one embodiment, the bacterium of the invention is a carboxydotroph.

The bacterium of the invention may be derived from the cluster of carboxydotrophic Clostridia comprising the species *Clostridium autoethanogenum, Clostridium ljungdahlii, Clostridium ragsdalei,* and related isolates, including, but not limited to, strains *Clostridium autoethanogenum* JAI-1T (DSM10061) (Abrini, *Arch Microbiol*, 161: 345-351, 1994), *Clostridium autoethanogenum* LBS1560 (DSM19630) (WO 2009/064200), *Clostridium autoethanogenum* LZ1561 (DSM23693), *Clostridium ljungdahlii* PETCT (DSM13528=ATCC 55383) (Tanner, *Int J Syst Bacteriol*, 43: 232-236, 1993), *Clostridium ljungdahlii* ERI-2 (ATCC 55380) (U.S. Pat. No. 5,593,886), *Clostridium ljungdahlii* C-01 (ATCC 55988) (U.S. Pat. No. 6,368,819), *Clostridium ljungdahlii* O-52 (ATCC 55989) (U.S. Pat. No. 6,368,819), *Clostridium ragsdalei* P11T (ATCC BAA-622) (WO 2008/028055), related isolates such as "*Clostridium coskatii*" (U.S. Publication 2011/0229947), or mutated strains such as *Clostridium ljungdahlii* OTA-1 (Tirado-Acevedo, Production of Bioethanol from Synthesis Gas Using *Clostridium ljungdahlii*, PhD thesis, North Carolina State University, 2010).

These strains form a subcluster within the Clostridial rRNA cluster I and their 16S rRNA gene is more than 99% identical with a similar low GC content of around 30%. However, DNA-DNA reassociation and DNA fingerprinting experiments showed that these strains belong to distinct species (WO 2008/028055). The strains of this cluster are defined by common characteristics, having both a similar genotype and phenotype, and they all share the same mode of energy conservation and fermentative metabolism. Furthermore, the strains of this cluster lack cytochromes and conserve energy via an Rnf complex. All species of this cluster have a similar morphology and size (logarithmic growing cells are between 0.5-0.7×3-5 µm), are mesophilic (optimal growth temperature between 30-37° C.), and are strictly anaerobic (Abrini, *Arch Microbiol*, 161: 345-351, 1994; Tanner, *Int J Syst Bacteriol*, 43: 232-236, 1993; and WO 2008/028055). Moreover, they all share the same major phylogenetic traits, such as same pH range (pH 4-7.5, with an optimal initial pH of 5.5-6), strong autotrophic growth on CO-containing gases with similar growth rates, and a similar metabolic profile with ethanol and acetic acid as main fermentation end products, and small amounts of 2,3-butanediol and lactic acid formed under certain conditions (Abrini, *Arch Microbiol*, 161: 345-351, 1994; Köpke, *Curr Opin Biotechnol*, 22: 320-325, 2011; Tanner, *Int J Syst Bacteriol*, 43: 232-236, 1993; and WO 2008/028055). Indole production was observed with all three species as well.

However, the species differentiate in substrate utilization of various sugars (e.g., rhamnose, arabinose), acids (e.g., gluconate, citrate), amino acids (e.g., arginine, histidine), or other substrates (e.g., betaine, butanol). Moreover some of the species were found to be auxotrophic to certain vitamins (e.g., thiamine, biotin) while others were not. The organization and number of Wood-Ljungdahl pathway genes, responsible for gas uptake, has been found to be the same in all species, despite differences in nucleic and amino acid sequences (Köpke, *Curr Opin Biotechnol*, 22: 320-325, 2011). Also, reduction of carboxylic acids into their corresponding alcohols has been shown in a range of these microorganisms (Perez, *Biotechnol Bioeng*, 110:1066-1077, 2012). These traits are therefore not specific to one microorganism, like *Clostridium autoethanogenum* or *Clostridium ljungdahlii*, but rather general traits for carboxydotrophic, ethanol-synthesizing Clostridia and it can be anticipated that mechanisms work similarly across these strains, although there may be differences in performance.

The term "substrate" refers to a carbon and/or energy source for the bacterium of the invention. Typically, the substrate is a gaseous substrate that comprises methane ($CH_4$). The bacterium of the invention generally converts at least a portion of the $CH_4$ in the substrate to a product. In one embodiment, $CH_4$ is the sole carbon source for the bacterium of the invention. The $CH_4$ may be sourced, for example, from natural gas, agriculture, landfills, wastewater, or biogas production plants.

Oftentimes, however, the substrate will also comprise carbon monoxide (CO). The substrate may comprise a major proportion of CO, such as about 20% to 99%, 20% to 70%, 30% to 60%, or 40% to 55% CO by volume. In particular embodiments, the substrate comprises about 25%, 30%, 35%, 40%, 45%, 50%, 55%, or 60% CO by volume.

While it is not necessary for the substrate to contain any hydrogen ($H_2$), the presence of $H_2$ should not be detrimental to product formation and may result in improved overall efficiency. For example, in particular embodiments, the substrate may comprise an approximate ratio of $H_2$:CO of 2:1, 1:1, or 1:2. In one embodiment, the substrate comprises less than about 30%, 20%, 15%, or 10% $H_2$ by volume. In other embodiments, the substrate comprises low concentrations of $H_2$, for example, less than 5%, less than 4%, less than 3%, less than 2%, or less than 1% $H_2$. In further embodiments, the substrate contains substantially no $H_2$. The substrate may also contain carbon dioxide ($CO_2$), for example, about 1% to 80% or 1% to 30% $CO_2$ by volume. In one embodiment, the substrate comprises less than about 20% $CO_2$ by volume. In further embodiments, the substrate comprises less than about 15%, 10%, or 5% $CO_2$ by volume. In another embodiment, the substrate contains substantially no $CO_2$.

In one embodiment, the substrate comprises $CH_4$ and one or more of CO, $CO_2$, and $H_2$. Existing methods are currently unable to utilize $CH_4$ and CO in parallel, although both gases are present in many gas streams. However, the invention provides a method of using a substrate comprising both $CH_4$ and CO and a microorganism capable of consuming such a substrate, e.g., an acetogenic bacterium that consumes a substrate comprising at least $CH_4$ and CO and converts at least a portion of the $CH_4$ and CO to a product. The substrate comprise a PSA tail gas, a gas stream generated from processes involving hydrogen production and purification. The PSA tail gas may comprise both $CH_4$ and CO. For example, the PSA tail gas may comprise approximately 12% CO, 25% $H_2$, 46% $CO_2$, and 17% $CH_4$. The substrate may comprise a steam methane reforming tail gas comprising both $CH_4$ and CO. For example, the steam methane reforming tail gas may comprise approximately 66% $H_2$, 9% $CO_2$, 22% CO, and 4% $CH_4$.

The substrate may be a waste gas obtained as a by-product of an industrial process or from some other source, such as from automobile exhaust fumes or biomass gasification. In certain embodiments, the industrial process is selected from the group consisting of ferrous metal products manufacturing, such as a steel mill manufacturing, non-ferrous products manufacturing, petroleum refining processes, coal gasification, electric power production, carbon black production, ammonia production, methanol production, and coke manufacturing. In these embodiments, the CO-containing gas may be captured from the industrial process before it is emitted into the atmosphere, using any convenient method. The CO may be a component of syngas, i.e., a gas comprising carbon monoxide and hydrogen. The CO produced from industrial processes is normally flared off to produce $CO_2$ and therefore the invention has particular utility in reducing $CO_2$ greenhouse gas emissions. The composition of the substrate may have a significant impact on the efficiency and/or cost of the reaction. For example, the presence of oxygen ($O_2$) may reduce the efficiency of an anaerobic fermentation process. Depending on the composition of the substrate, it may be desirable to treat, scrub, or filter the substrate to remove any undesired impurities, such as toxins, undesired components, or dust particles, and/or increase the concentration of desirable components.

The substrate may also be a blend of individual substrates. For example, the substrate may be obtained by blending a gaseous substrate comprising $CH_4$ with a gaseous substrate comprising one or more of CO, $CO_2$, and $H_2$.

Additionally, the substrate may comprise one or more of nitric oxide (NO), nitrite ($NO_2^-$) and nitrate ($NO_3^-$). NO is required as substrate for NOD that catalyzes the reaction of two molecules of NO into $N_2$ and $O_2$. The $O_2$ can then be immediately used for methane oxidation by the MMO. Nitric oxide itself can be derived from $NO_2^-$ by NIR, which catalyzes the reduction of $NO_2^-$ to NO. $NO_2^-$ can be derived from $NO_3^-$ by nitrate reductase which catalyses the reduction of $NO_3^-$ to $NO_2^-$.

Although the substrate is typically gaseous, the substrate may also be provided in alternative forms. For example, the substrate may be dissolved in a liquid saturated with a CO-containing gas using a microbubble dispersion generator (Hensirisak, *Appl Biochem Biotechnol*, 101: 211-227, 2002). By way of further example, the substrate may be adsorbed onto a solid support. Moreover, certain components of the substrate (e.g., $CH_4$, CO, $CO_2$, and/or $H_2$) may be provided in gaseous form while other components of the substrate (e.g., $NO_2^-$ and/or nitrate $NO_3^-$) may be provided in liquid form.

The bacterium of the invention may be cultured to produce one or more products. Typically, the culture is performed in a bioreactor. The term "bioreactor" includes a culture/fermentation device consisting of one or more vessels, towers, or piping arrangements, such as a continuous stirred tank reactor (CSTR), immobilized cell reactor (ICR), trickle bed reactor (TBR), bubble column, gas lift fermenter, static mixer, or other vessel or other device suitable for gas-liquid contact. In some embodiments, the bioreactor may comprise a first growth reactor and a second culture/fermentation reactor. The substrate may be provided to one or both of these reactors. As used herein, the terms "culture" and "fermentation" are used interchangeably. These terms encompass both the growth phase and product biosynthesis phase of the culture/fermentation process.

The culture is generally maintained in an aqueous culture medium that contains nutrients, vitamins, and/or minerals sufficient to permit growth of the bacterium. Preferably the aqueous culture medium is a minimal anaerobic microbial growth medium. Suitable media are known in the art and described, for example, in U.S. Pat. No. 5,173,429, U.S. Pat. No. 5,593,886, and WO 2002/008438.

The culture/fermentation should desirably be carried out under appropriate conditions for production of the target product. Reaction conditions to consider include pressure (or partial pressure of CO), temperature, gas flow rate, liquid flow rate, media pH, media redox potential, agitation rate (if using a continuous stirred tank reactor), inoculum level, maximum gas substrate concentrations to ensure that CO in the liquid phase does not become limiting, and maximum product concentrations to avoid product inhibition. In particular, the rate of introduction of the CO-containing substrate may be controlled to ensure that the concentration of CO in the liquid phase does not become limiting, since products may be consumed by the culture under CO-limited conditions.

Operating a bioreactor at elevated pressures allows for an increased rate of gas mass transfer from the gas phase to the liquid phase. Accordingly, it is generally preferable to perform the culture/fermentation at pressures higher than atmospheric pressure. Also, since a given gas conversion rate is, in part, a function of the substrate retention time and retention time dictates the required volume of a bioreactor, the use of pressurized systems can greatly reduce the volume of the bioreactor required and, consequently, the capital cost of the culture/fermentation equipment. According to examples in U.S. Pat. No. 5,593,886, reactor volume can be reduced in linear proportion to increases in reactor operating pressure. In other words, a bioreactor operated at 10 atmospheres of pressure need only be one tenth the volume of a bioreactor operated at 1 atmosphere of pressure. Additionally, WO 2002/008438 describes gas-to-ethanol fermentations performed under pressures of 30 psig and 75 psig, giving ethanol productivities of 150 g/L/day and 369 g/L/day, respectively. In contrast, fermentations performed using similar media and input gas compositions at atmospheric pressure were found to produce between 10 and 20 times less ethanol per liter per day.

The bacterium of the invention may produce or be engineered to produce a wide variety of products. For example, the products may comprise one or more of ethanol (WO 2007/117157), acetate (WO 2007/117157), butanol (WO 2008/115080 and WO 2012/053905), butyrate (WO 2008/115080), 2,3-butanediol (WO 2009/151342), lactate (WO 2011/112103), butene (WO 2012/024522), butadiene (WO 2012/024522), methyl ethyl ketone (2-butanone) (WO 2012/024522 and WO 2013/185123), ethylene (WO 2012/026833), acetone (WO 2012/115527), isopropanol (WO 2012/115527), lipids (WO 2013/036147), 3-hydroxypropionate (3-HP) (WO 2013/180581), isoprene (WO 2013/180584), fatty acids (WO 2013/191567), 2-butanol (WO 2013/185123), 1,2-propanediol (WO 2014/0369152), and 1-propanol (WO 2014/0369152).

EXAMPLES

The following examples further illustrate the invention but, of course, should not be construed to limit its scope in any way.

Example 1

This example demonstrates the feasible conversion of methane to a target product using a recombinant acetogenic bacterium.

A genome-scale metabolic model of *C. autoethanogenum* similar to the one described by Marcellin (Low carbon fuels and commodity chemicals from waste gases—Systematic approach to understand energy metabolism in a model acetogen, *Green Chem*, 2016) was utilized. Metabolic reactions representing MMO, NIR and NOD were added to this genome-scale model.

Growth was simulated by flux balance analysis (FBA), using scripts from the COBRA Toolbox v2.0 in MATLAB R2014a (The Mathworks, Inc.) with Gurobi version 6.0.4 as the solver (Gurobi Optimization, Inc.). Exchange reactions were constrained to represent a minimal growth medium supplemented with nitrite. FBA predicts that methane can be utilized as a growth substrate by the recombinant *C. autoethanogenum*; the results are illustrated in Table 1.

The maximum theoretical yield of ethanol, an example product, was calculated using FBA. These results illustrate the feasible conversion of methane to a target product using the recombinant *C. autoethanogenum*.

TABLE 1

Flux balance analysis (FBA) of *C. autoethanogenum* growth using methane as a substrate, with MMO, NIR and NOD and two routes for methanol assimilation.

| Route for methanol assimilation | Methane uptake rate (mmol $CH_4$/gDW/hour) | CO uptake rate (mmol CO/gDW/hour) | Specific growth rate (1/hour) | Combined ethanol and acetate production rate (mmol ethanol and acetate/gDW/hour) | Maximum ethanol (mmol CO/gDW/hour) |
|---|---|---|---|---|---|
| Wild type | 0 | 60 | 0.136 | 10.3 | 10.0 |
| Methanol methyltransferase | 15 | 60 | 0.203 | 12.9 | 7.50 |
| Oxidation of methanol to formate | 10 | 60 | 0.073 | 10.4 | 11.7 |

All references, including publications, patent applications, and patents, cited herein are hereby incorporated by reference to the same extent as if each reference were individually and specifically indicated to be incorporated by reference and were set forth in its entirety herein. The reference to any prior art in this specification is not, and should not be taken as, an acknowledgment that that prior art forms part of the common general knowledge in the field of endeavour in any country.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A recombinant bacterium that consumes a substrate comprising $CH_4$ and converts at least a portion of the $CH_4$ to a product, wherein the bacterium comprises a Wood-Ljungdahl pathway and comprises exogenous *Methylomirabilis oxyfera* methane monooxygenase (MMO).

2. The bacterium of claim 1, wherein the bacterium further comprises exogenous nitrite reductase (NIR) and/or exogenous nitric oxide dismutase (NOD).

3. The bacterium of claim 2, wherein the nitrite reductase is *Methylomirabilis oxyfera* nitrite reductase and/or the nitric oxide dismutase is *Methylomirabilis oxyfera* nitric oxide dismutase.

4. The bacterium of claim 2, wherein the bacterium further comprises exogenous methanol methyltransferase.

5. The bacterium of claim 1, wherein the bacterium is a member of genus *Clostridium* or *Acetobacterium*.

6. The bacterium of claim 1, wherein the bacterium is derived from *Clostridium autoethanogenum, Clostridium ljungdahlii, Clostridium ragsdalei,* or *Acetobacterium woodii.*

7. The bacterium of claim 1, wherein the substrate further comprises one or more of CO, $CO_2$, and $H_2$.

8. The bacterium of claim 1, wherein the substrate further comprises one or more of $NO_2^-$ and $NO_3^-$.

9. The bacterium of claim 1, wherein $CH_4$ is the sole carbon source for the bacterium.

10. The bacterium of claim 1, wherein the product comprises one or more of ethanol, acetate, butanol, butyrate, 2,3-butanediol, lactate, butene, butadiene, methyl ethyl ketone (2-butanone), ethylene, acetone, isopropanol, lipids, 3-hydroxypropionate (3-HP), isoprene, fatty acids, 2-butanol, 1,2-propanediol, and 1-propanol.

11. A method for producing a product comprising providing a substrate comprising $CH_4$ to a culture comprising the bacterium of claim 1, whereby the bacterium converts at least a portion of the $CH_4$ to a product.

12. The method of claim 11, wherein the bacterium further comprises exogenous nitrite reductase (NIR) and/or exogenous nitric oxide dismutase (NOD).

13. The method of claim 12, wherein the nitrite reductase is *Methylomirabilis oxyfera* nitrite reductase, and/or the nitric oxide dismutase is *Methylomirabilis oxyfera* nitric oxide dismutase.

14. The method of claim 12, wherein the bacterium further comprises methanol methyltransferase.

15. The method of claim 11, wherein the bacterium is a member of genus *Clostridium* or *Acetobacterium*.

16. The method of claim 11, wherein the bacterium is derived from *Clostridium autoethanogenum, Clostridium ljungdahlii, Clostridium ragsdalei*, or *Acetobacterium woodii*.

17. The method of claim 11, wherein the substrate further comprises one or more of CO, $CO_2$, and $H_2$.

18. The method of claim 11, wherein the substrate further comprises one or more of $NO_2^-$ and $NO_3^-$.

19. The method of claim 11, wherein $CH_4$ is the sole carbon source for the bacterium.

20. The method of claim 11, wherein the product comprises one or more of ethanol, acetate, butanol, butyrate, 2,3-butanediol, lactate, butene, butadiene, methyl ethyl ketone (2-butanone), ethylene, acetone, isopropanol, lipids, 3-hydroxypropionate (3-HP), isoprene, fatty acids, 2-butanol, 1,2-propanediol, and 1-propanol.

\* \* \* \* \*

SEQUENCE LISTING

```
<160> NUMBER OF SEQ ID NOS: 26

<210> SEQ ID NO 1
<211> LENGTH: 243
<212> TYPE: PRT
<213> ORGANISM: Methylomirabilis oxyfera

<400> SEQUENCE: 1

Met Ala Leu Leu Thr Gln Gln Ala Leu Ser Leu Glu Arg Lys Phe
1               5                   10                  15

Asp Ile Ile Val Ile Val Ala Ala Phe Thr Gly Thr Val Ala Gly Tyr
                20                  25                  30

His Ile His Gln Met Leu Thr Val Gly Asp Trp Asp Phe Trp Leu Asp
            35                  40                  45

Trp Lys Asp Arg Arg Trp Trp Val Thr Leu Thr Pro Ile Leu Leu Ile
    50                  55                  60

Thr Phe Pro Ala Ala Thr Gln Tyr Phe Met Trp Glu Lys Met Arg Leu
65                  70                  75                  80

Pro Ile Gly Ala Thr Phe Cys Val Met Thr Leu His Phe Gly Gln Trp
                85                  90                  95

Met Asn Arg Val Phe Asn Phe Tyr Tyr Trp Ala Trp Phe Pro Val Asn
                100                 105                 110

Phe Thr Ala Pro Gly Leu Met Ile Pro Ser Ala Ile Phe Leu Asp Val
            115                 120                 125

Met Leu Met Met Thr Gly Ser Tyr Met Phe Thr Ala Leu Phe Gly Gly
        130                 135                 140

Met Gly Trp Ser Leu Leu Phe Tyr Pro Ala Asn Trp Thr Trp Leu Ala
145                 150                 155                 160

Pro Phe His Leu Ala Val Lys His Pro Ser Gly Pro Leu Met Ser Ile
                165                 170                 175

Ala Asp Leu Met Gly Met Glu Tyr Val Arg Ser Ala Thr Pro Glu Tyr
                180                 185                 190

Ile Arg Ile Val Glu Arg Gly Thr Leu Arg Thr Phe Gly Arg Asp Val
            195                 200                 205

Thr Pro Val Ser Ser Phe Phe Ala Gly Phe Ile Ser Gly Ile Ile Tyr
        210                 215                 220

Leu Trp Trp Val Trp Met Gly Lys Val Ile Ser Arg Pro Ala Trp Ile
225                 230                 235                 240

Ser Arg Thr

<210> SEQ ID NO 2
<211> LENGTH: 732
<212> TYPE: DNA
<213> ORGANISM: Methylomirabilis oxyfera

<400> SEQUENCE: 2
atggcgcttt tgacacaaca gcaagctcta agcctggagc gcaagtttga tattattgtc      60
```

-continued

| | |
|---|---|
| atagtggctg cgttcacagg tacagttgcg gggtaccaca tccaccagat gctgaccgtt | 120 |
| ggcgactggg acttctggct ggactggaag gatcggcgct ggtgggtcac gttgacgccg | 180 |
| atcctgttga ttaccttccc tgcggcgacg caatatttca tgtgggagaa gatgcgtctg | 240 |
| ccgatcggtg cgacctttg cgtgatgacg cttcacttcg acaatggat gaatcgtgtc | 300 |
| tttaactttt actattgggc ctggtttccg gtcaatttta ccgccccggg tctgatgatc | 360 |
| cccagtgcga tcttcctgga cgtgatgctg atgatgacgg gaagctacat gtttacggca | 420 |
| ctgttcggtg gcatggggtg gtccctgttg ttctatccgg cgaactggac ctggctggcg | 480 |
| ccatttcatt tggccgtgaa gcatcccagc gggccgctca tgtccatcgc tgatctgatg | 540 |
| gggatggagt atgtgcgctc cgccacgccg gagtatatcc gaatcgtgga gcggggacg | 600 |
| ctgcgaacat cgggcgcga cgttacgccg gtttcctcgt tcttcgccgg atttattagt | 660 |
| ggaattatct acctctggtg ggtgtggatg gggaaggtaa tctcaaggcc ggcatggatc | 720 |
| tcgcggacgt ag | 732 |

<210> SEQ ID NO 3
<211> LENGTH: 422
<212> TYPE: PRT
<213> ORGANISM: Methylomirabilis oxyfera

<400> SEQUENCE: 3

```
Met Arg Ile Gly Arg Ala Ala Leu Ser Ala Ile Leu Leu Gly Val Ile
1               5                   10                  15

Ala Val Ser Ala Gly Thr Ala Trp Ala His Gly Glu Arg Ser Gln Glu
                20                  25                  30

Pro Phe Leu Arg Met Arg Thr Ile Thr Phe Tyr Asp Thr Lys Trp Ser
            35                  40                  45

Lys Ala Arg Val Gln Pro Gly Glu Thr Met Asp Leu Thr Gly Lys Phe
        50                  55                  60

His Thr Phe Ser Glu Trp Pro Arg Ala Val Asn Thr Pro Glu Ser Ile
65                  70                  75                  80

Phe Leu His Tyr Ser Val Pro Gly Pro Ser Met Leu Lys Lys Glu Ala
                85                  90                  95

Trp Met Asn Gly Met Pro Val Ile Asn Ala Thr Ser Thr Gln Leu Gly
                100                 105                 110

Gly Asp Tyr Asp Tyr Arg Met Asn Ile Met Gly Arg Val Thr Gly Thr
            115                 120                 125

Tyr His Val His Pro Met Val Asn Ile Glu Gly Gly Pro Leu Val
        130                 135                 140

Gly Gly Gly Glu Phe Val Thr Val Asp Gly Asp Trp Ser Asn Phe Thr
145                 150                 155                 160

Asn Asn Val Thr Thr Ile Asp Gly Thr Thr Val Asn Met Glu Val His
                165                 170                 175

Gly Gln Gly Arg Ile Ile Gly Trp Trp Leu Leu Trp Thr Phe Val Gly
            180                 185                 190

Val Phe Trp Leu Leu Trp Trp Val Arg Arg Pro Phe Thr Arg Arg Leu
        195                 200                 205

Phe Gln Val Gly Val Val Pro Glu Glu Glu Leu Val Ser Pro Gly Asp
    210                 215                 220

Arg Thr Leu Gly Leu Val Leu Met Ile Ala Thr Val Leu Ile Val Ala
225                 230                 235                 240

Ile Gly Tyr Val Thr Thr Asn Gly Ala Tyr Pro Ile Thr Ile Pro Leu
                245                 250                 255
```

```
Gln Thr Gly Arg Met Asp Thr Pro Glu Leu Lys Pro Thr Thr Glu Phe
            260                 265                 270

Thr Pro Tyr Ser His Ala Thr Val Lys Ala Arg Pro Val Thr Ala Val
        275                 280                 285

Tyr Thr Val Pro Gly Arg Ser Leu Gly Met Val Ile Glu Val Thr Asn
    290                 295                 300

Gly Ser Asn Arg Pro Gln Gln Leu Gly Gly Phe Ile Thr Ala Asn Leu
305                 310                 315                 320

Gln Phe Arg Asp Pro Ala Leu Phe Pro Asp Ser Arg Leu Lys Ile Lys
                325                 330                 335

Val Glu Pro Ala Gly Pro Ile Pro Pro Gly Gln Thr Val Thr Met Ser
            340                 345                 350

Ile Asp Ala Thr Asp Ala Glu Trp Glu Tyr Gln Arg Leu Ala Glu Leu
        355                 360                 365

Ile Tyr Asp Ser Asp Ser Arg Tyr Gly Gly Leu Phe Glu Phe Phe Asp
    370                 375                 380

Ala Asp Lys Asn Arg Gln Ile Val Glu Val Gly Gly Pro Val Ile Pro
385                 390                 395                 400

Ser Phe Glu Gly Gly Ala Thr Ala Leu Ser Gly Gly Gly Lys Trp Arg
                405                 410                 415

Pro Thr Thr Gln Tyr Lys
            420

<210> SEQ ID NO 4
<211> LENGTH: 1269
<212> TYPE: DNA
<213> ORGANISM: Methylomirabilis oxyfera

<400> SEQUENCE: 4
atgaggatag gacgagcggc gttgtcggcg atcttgcttg gagtgatcgc cgtatccgct      60
ggaacggcat gggcgcatgg cgagcgatcg caagagccgt tcttcggat gcgtacaata     120
acgttctacg atacgaaatg gtcaaaagct cgggtacagc ctggcgagac catggatctg     180
acgggaaagt tccatacatt tagtgaatgg ccgagggccg taaacacccc cgaatcgatc     240
tttctccatt actccgtgcc tgggccatca atgctcaaga agaggcatg gatgaatggc     300
atgccggtca tcaacgccac cagtactcaa cttggcggag actatgatta tagaatgaat     360
attatgggcc gggtcaccgg gacctatcac gttcacccga tggtgaatat cgagggtgga     420
gggcccctgg tcggtggagg cgagttcgtc accgtcgatg cgactggag taacttcacc     480
aataacgtta ccaccattga tggtacgaca gtgaatatgg aggtccatgg gcaaggtcgg     540
atcatcggct ggtggctcct ctggactttt gtcggtgtgt tctggttgct gtggtgggta     600
cgacggccat ttacgcgacg tctcttccag gtgggagtgg tacctgagga ggagcttgtt     660
agccccggcg atcggacgct tggactcgta ctgatgatcg ccacggtcct catcgtcgct     720
atcggctacg tcacgacgaa cggcgcctac ccaatcacca tcccgctgca gaccggtcgg     780
atggatactc ccgaactgaa gcccacgaca gagtttacgc cgtattccca tgccacggtg     840
aaggccaggc ctgtcacagc ggtctatacc gtacctggac gttctcttgg gatggtgata     900
gaggtcacaa acggttcaaa caggcctcag caattgggag gattcatcac ggccaacctg     960
cagtttcggg atccgccct cttccctgac tcgcgactca aaatcaaggt ggagccggcc    1020
ggtcccatcc ctccaggcca gaccgtaacg atgtcgatag atgcgaccga tgcggaatgg    1080
gaatatcagc ggttggctga gttgatctat gactcagaca gccggtacgg cggactcttt    1140
```

```
gagttctttg atgcggataa gaacagacaa attgttgagg tcggcggccc ggtcattccg    1200
tccttcgagg gtggcgcaac ggccctgtcc ggcggaggca aatggcggcc gactacccag    1260
tacaaatag                                                            1269
```

<210> SEQ ID NO 5
<211> LENGTH: 258
<212> TYPE: PRT
<213> ORGANISM: Methylomirabilis oxyfera

<400> SEQUENCE: 5

```
Met Ala Gln Tyr Arg Thr Glu Ala Ala Pro Ala Lys Arg Ala Glu Ser
1               5                   10                  15

Val Glu Gln Met Phe Gly Trp Gly Thr Phe Phe Lys Cys Gln Ile Ala
            20                  25                  30

Ile Ser Ile Phe Tyr Val Met Ile Arg Ile Tyr Gln Gln Tyr Phe Ser
        35                  40                  45

Trp Ser Lys Gly Leu Asp Phe Phe Ser Glu Asp Phe Arg Ile Tyr Trp
    50                  55                  60

Trp Asn Met Leu Ile Gly Glu Leu Ile Ile Glu Gly Ala Val Leu Thr
65                  70                  75                  80

Phe Ala Leu Gly Tyr Ile Trp Lys Thr Arg Asp Arg Asn Leu Asp Lys
                85                  90                  95

Ile Thr Pro Glu Glu Leu Arg Arg Phe Trp Gly Leu Gly Gln Trp
            100                 105                 110

Ile Ala Thr Phe Ala Trp Ala Val Tyr Trp Gly Ala Ser Phe Phe Thr
        115                 120                 125

Glu Gln Asp Gly Thr Trp His Gln Thr Val Ile Arg Asp Thr Asp Phe
    130                 135                 140

Thr Pro Ser His Ile Ile Glu Phe Tyr Leu Ser Tyr Pro Ile Tyr Ile
145                 150                 155                 160

Ile Ile Gly Ile Ser Ala Tyr Met Trp Ala Arg Thr Arg Leu Pro Leu
                165                 170                 175

Phe Ser Lys Ala His Ser Ile Pro Phe Met Leu Thr Val Gly Gly Pro
            180                 185                 190

Ala Met Ile Phe Val Asn Val Ala Leu Asn Glu Trp Gly His Thr Phe
        195                 200                 205

Trp Ile Met Glu Glu Leu Phe Val Ala Pro Leu His Trp Gly Phe Val
    210                 215                 220

Thr Leu Gly Trp Cys Leu Phe Gly Val Tyr Gly Val Ala Ala Ala Met
225                 230                 235                 240

Cys Pro Arg Ile Phe Glu Leu Ile Arg Ile Thr Ser Gly Gly Lys Ala
                245                 250                 255

Thr Ala
```

<210> SEQ ID NO 6
<211> LENGTH: 777
<212> TYPE: DNA
<213> ORGANISM: Methylomirabilis oxyfera

<400> SEQUENCE: 6

```
atggcacagt acaggacgga agctgcgccg gctaagcgcg ccgagtcagt cgagcagatg    60
tttggctggg gcaccttctt taaatgtcag atagctatta gcatcttcta cgttatgatt    120
cggatttacc agcagtactt ctcctggtcg aaaggcctcg acttcttctc cgaggacttc    180
```

```
cggatctact ggtggaacat gttgatcggg gagttgatta tcgagggggc ggtgctgacc      240
ttcgccctgg ggtacatctg gaagactcgc gaccggaacc tcgataaaat tacgccggag      300
gaggagctca ggcggttctg gggtctcggg cagtggatcg cgacgttcgc ctgggcggtg      360
tattggggcg ccagcttctt taccgagcag gacgggacgt ggcaccagac ggtgatccgc      420
gatacggact ttacgccgag ccacatcatt gagttctatc tcagctaccc gatctacatc      480
atcatcggga ttagcgccta catgtgggcc cggacccgac tccccctatt ttcgaaggcc      540
cactcgatcc cgttcatgct cacggtcggc ggccctgcga tgatctttgt caatgtcgcg      600
ctgaacgagt ggggtcacac cttctggatc atggaagagc tgtttgtggc gccgctgcat      660
tggggctttg tcacgctggg ttggtgtctg tttggggtgt atggcgtggc ggcggcgatg      720
tgtccgcgga tctttgagtt gatcaggatc accagcggtg gtaaggcgac cgcgtaa      777
```

<210> SEQ ID NO 7
<211> LENGTH: 258
<212> TYPE: PRT
<213> ORGANISM: Methylomirabilis oxyfera
<400> SEQUENCE: 7

```
Met Ala Gln Tyr Arg Thr Glu Ala Ala Pro Ala Lys Arg Ala Glu Ser
1               5                   10                  15

Val Glu Gln Met Phe Gly Trp Gly Thr Phe Lys Cys Gln Ile Ala
            20                  25                  30

Ile Ser Ile Phe Tyr Val Met Ile Arg Ile Tyr Gln Gln Tyr Phe Ser
        35                  40                  45

Trp Ser Lys Gly Leu Asp Phe Phe Ser Glu Asp Phe Arg Ile Tyr Trp
    50                  55                  60

Trp Asn Met Leu Ile Gly Glu Leu Ile Ile Glu Gly Ala Val Leu Thr
65                  70                  75                  80

Phe Ala Leu Gly Tyr Ile Trp Lys Thr Arg Asp Arg Asn Leu Asp Lys
                85                  90                  95

Ile Thr Pro Glu Glu Glu Leu Arg Arg Phe Trp Gly Leu Gly Gln Trp
            100                 105                 110

Ile Ala Thr Phe Ala Trp Ala Val Tyr Trp Gly Ala Ser Phe Phe Thr
        115                 120                 125

Glu Gln Asp Gly Thr Trp His Gln Thr Val Ile Arg Asp Thr Asp Phe
    130                 135                 140

Thr Pro Ser His Ile Ile Glu Phe Tyr Leu Ser Tyr Pro Ile Tyr Ile
145                 150                 155                 160

Ile Ile Gly Ile Ser Ala Tyr Met Trp Ala Arg Thr Arg Leu Pro Leu
                165                 170                 175

Phe Ser Lys Ala His Ser Ile Pro Phe Met Leu Thr Val Gly Gly Pro
            180                 185                 190

Ala Met Ile Phe Val Asn Val Ala Leu Asn Glu Trp Gly His Thr Phe
        195                 200                 205

Trp Ile Met Glu Glu Leu Phe Val Ala Pro Leu His Trp Gly Phe Val
    210                 215                 220

Thr Leu Gly Trp Cys Leu Phe Gly Val Tyr Gly Val Ala Ala Ala Met
225                 230                 235                 240

Cys Pro Arg Ile Phe Glu Leu Ile Arg Ile Thr Ser Gly Gly Lys Ala
                245                 250                 255

Thr Ala
```

```
<210> SEQ ID NO 8
<211> LENGTH: 777
<212> TYPE: DNA
<213> ORGANISM: Methylomirabilis oxyfera

<400> SEQUENCE: 8
atggcacagt acaggacgga agctgcgccg gctaagcgcg ccgagtcagt cgagcagatg      60
tttggctggg gcaccttctt taaatgtcag atagctatta gcatcttcta cgttatgatt     120
cggatttacc agcagtactt ctcctggtcg aaaggcctcg acttcttctc cgaggacttc     180
cggatctact ggtggaacat gttgatcggg gagttgatta tcgaggggc ggtgctgacc      240 ttcgccctgg ggtacatctg gaagactcgc gaccggaacc tcgataaaat tacgccggag     300
gaggagctca gcggttctg gggtctcggg cagtggatcg cgacgttcgc ctgggcggtg      360
tattggggcg ccagcttctt taccgagcag gacgggacgt ggcaccagac ggtgatccgc     420
gatacggact ttacgccgag ccacatcatt gagttctatc tcagctaccc gatctacatc     480
atcatcggga ttagcgccta catgtgggcc cggacccgac tcccctatt ttcgaaggcc      540 cactcgatcc cgttcatgct cacggtcggc ggccctgcga tgatctttgt caatgtcgcg     600
ctgaacgagt ggggtcacac cttctggatc atggaagagc tgtttgtggc gccgctgcat     660
tggggctttg tcacgctggg ttggtgtctg tttggggtgt atggcgtggc ggcggcgatg     720
tgtccgcgga tctttgagtt gatcaggatc accagcggtg gtaaggcgac cgcgtaa       777

<210> SEQ ID NO 9
<211> LENGTH: 546
<212> TYPE: PRT
<213> ORGANISM: Methylomirabilis oxyfera

<400> SEQUENCE: 9

Met Thr Thr Arg Thr Lys Leu Thr Val Leu Thr Val Ala Leu Gly Met
1               5                   10                  15

Leu Trp Thr Val Pro Val Leu Ala Ala Glu Ala Pro Pro Ala Leu Pro
            20                  25                  30

Pro Ala Pro Pro Leu Ala Pro Gly Glu Leu Glu Ala Ala Lys Gln Ile
        35                  40                  45

Tyr Phe Asp Arg Cys Ala Gly Cys His Gly Val Leu Arg Lys Gly Ala
    50                  55                  60

Thr Gly Pro Gln Leu Leu Pro Ala Lys Thr Arg Ala Leu Thr Thr Pro
65                  70                  75                  80

Val Leu Lys Ala Phe Ile Val Asn Gly Thr Gly Gly Met Pro Asp
            85                  90                  95

Trp Gly Arg Gln Gly Ile Leu Thr Asp Ala Glu Ser Asp Leu Met Ala
            100                 105                 110

Arg Tyr Ile Gln His Asp Pro Pro Thr Pro Glu Leu Ser Met Ala
        115                 120                 125

Asp Met Lys Lys Ser Trp Asn Leu Ile Val Pro Pro Asp Lys Arg Pro
130                 135                 140

Thr Lys Pro Glu His Asn Arg Asp Trp Gln Asn Phe Phe Ala Val Thr
145                 150                 155                 160

Leu Arg Asp Ala Gly Gln Val Ala Ile Ile Asp Gly Thr Lys Glu
            165                 170                 175

Ile Val Asn Thr Val Lys Thr Gly Phe Ala Val His Ile Ser Arg Ser
        180                 185                 190

Ser Phe Ser Gly Arg Tyr Met Tyr Thr Ile Gly Arg Asp Gly Arg Ala
    195                 200                 205
```

```
Thr Met Ile Asp Leu Trp Met Lys Val Pro Asp Lys Ile Ala Glu Ile
    210                 215                 220
Lys Pro Cys Ser Asp Ala Arg Ser Ile Asp Thr Ser Lys Tyr Lys Gly
225                 230                 235                 240
Lys Leu Gly Asp Phe Thr Asp Lys Leu Ala Val Ile Gly Cys Tyr Trp
                245                 250                 255
Pro Pro Gln Ile Ile Val Thr Asp Gly Asn Thr Leu Glu Pro Leu Lys
                260                 265                 270
Val Ile Ser Ser Arg Ser Met Thr Tyr Asp Thr Met Glu Tyr His Pro
            275                 280                 285
Glu Pro Arg Val Ala Ser Ile Val Ala Ser His Phe Lys Pro Glu Trp
290                 295                 300
Val Ile Asn Ile Lys Glu Thr Gly Leu Ile Trp Leu Val Asp Tyr Ser
305                 310                 315                 320
Asp Leu Lys Asn Leu Lys Met Thr Gln Ile Gln Gly Glu Lys Phe Leu
                325                 330                 335
His Asp Gly Gly Trp Asp Ser Thr Lys Arg Tyr Phe Met Val Ala Ala
                340                 345                 350
Asn Met Ala Asn Lys Val Val Val Ile Asp Val Glu Lys Gly Lys Leu
            355                 360                 365
Glu Ala Ile Phe Glu Ser Gly Ile Lys Pro His Pro Gly Arg Gly Ala
370                 375                 380
Asn Trp Ile Asp Pro Lys Phe Gly Pro Val Asn Gly Thr Pro His Leu
385                 390                 395                 400
Gly Glu Gly Lys Ile Ala Val Tyr Gly Thr Asp Pro Ala Lys His Lys
                405                 410                 415
Glu Ser Ala Trp Lys Lys Val Arg Asp Leu Lys Thr Leu Gly Gly Gly
                420                 425                 430
Gly Leu Phe Ile Lys Thr His Pro Lys Ser Lys Asn Val Trp Val Asp
            435                 440                 445
His Ala Leu Asn Gly Asp Pro Ala Ile Gln Lys Gln Val Cys Val Phe
450                 455                 460
Glu Lys Ala Asn Pro Glu Lys Asp Pro Lys Cys Trp Lys Val Ser Asp
465                 470                 475                 480
Lys Gly Arg Ala Val His Phe Glu Phe Asn Lys Ala Gly Asp Glu Val
                485                 490                 495
Trp Ile Ser Val Trp Gly Lys Lys Asp Gly Lys Ser Glu Ile Val Val
                500                 505                 510
Tyr Asp Asp Lys Thr Leu Gln Glu Lys Ala Arg Ile Asp Asp Pro Arg
            515                 520                 525
Ile Ile Thr Pro Thr Gly Lys Phe Asn Val Tyr Asn Thr Val Lys Asp
530                 535                 540
Ile Tyr
545
```

<210> SEQ ID NO 10
<211> LENGTH: 1641
<212> TYPE: DNA
<213> ORGANISM: Methylomirabilis oxyfera

<400> SEQUENCE: 10

```
atgacgacta gaacaaagtt gacggtgtta actgtggcgc taggcatgct atggaccgtt    60
ccggttctgg ctgcggaggc gccgccggcg cttccaccgg ctccaccgct ggcccctggc   120
```

-continued

```
gaacttgagg cggccaagca gatctatttc gaccggtgcg cgggctgtca cggggtcttg    180
agaaaaggtg caaccggtcc gcagcttctg ccggcaaaaa cccgcgcttt gactacaccg    240
gttttgaaag cgttcatcgt gaatggtacg ggaggcggga tgccggactg gggtcggcaa    300
ggcattctca ccgacgccga aagcgacctg atggcccgtt acatccagca tgacccgccc    360
acacctcccg agctctctat ggcggatatg aagaaaagct ggaacctgat cgtgccgccg    420
gataagcgac ccacgaagcc agaacataac cgtgactggc agaacttttt cgccgtgacc    480
cttcgtgacg ccggtcaggt ggcgatcatc gacggcgata ccaaagagat cgtcaacacg    540
gtcaagacgg ggtttgcggt ccatatctcg cgcagttcct tttcgggacg ctacatgtat    600
actatcggcc gtgatggtcg ggcgacgatg atcgatctgt ggatgaaggt tccggataag    660
atcgcggaga tcaaaccgtg cagcgatgcg cgctctatcg atacgagtaa gtataaaggt    720
aagctcggtg acttcaccga caagctggcc gtcatcggtt gctattggcc gccgcagatt    780
attgtgacgg acggtaacac gctggaacca ctgaaggtca tcagcagtcg gagcatgacc    840
tacgatacga tggagtatca ccccgagccc cgggtcgcct cgatcgtggc gtcgcacttc    900
aagcccgagt gggtcattaa cattaaggag accgggctga tctggcttgt cgattactcg    960
gatctcaaga acctcaagat gacccagatc caaggcgaga gtttctgca cgacggcggc   1020 tgggacagca ccaaacgcta cttcatggtg gcggctaaca tggcgaacaa ggtggtcgtg   1080
atcgacgtcg agaagggtaa gctggaggcg atcttcgaat ccggaatcaa gcctcatccg   1140
ggacgtggcg ccaactggat cgatccgaaa ttcggtccgg tgaatggtac cccgcatctc   1200
ggcgaaggca agatcgccgt ttacggtacc gatccggcca agcacaagga gtctgcctgg   1260
aaaaaggtga gggatctcaa gacgctcgga ggaggcggcc tgtttatcaa gacgcacccg   1320
aagagtaaaa atgtctgggt agatcacgcc ctgaatggcg atccagccat tcaaaagcag   1380
gtctgcgttt tcgagaaagc gaatccggag aaagatccga agtgctggaa ggtatcggac   1440
aaaggtcgcg ctgtgcattt cgagttcaat aaggccgggg atgaggtgtg gatcagcgtc   1500
tgggggaaga agacggcaa gagcgagatc gtcgtgtatg atgataagac actgcaagag   1560
aaggccagga tcgacgatcc gcgcatcatc acgccgacag gtaagtttaa cgtctacaac   1620
actgtgaagg atatttatta a                                            1641
```

<210> SEQ ID NO 11
<211> LENGTH: 808
<212> TYPE: PRT
<213> ORGANISM: Methylomirabilis oxyfera

<400> SEQUENCE: 11

```
Met Arg Ser Ser Ser Ser Gly Met Gly Lys Thr Asn Arg Thr Phe
1               5                   10                  15

Gly Gln Ala Leu Leu Ile Lys Lys Tyr Trp Trp Leu His Ala Leu Ile
            20                  25                  30

Val Thr Val Ile Ser Val Ile Gly Leu Val Ala Leu Gly Val Trp Thr
        35                  40                  45

Tyr Thr Ser Ala Pro Pro Leu Thr Asn Tyr Val Leu Ser Ser Thr Gly
    50                  55                  60

Glu Thr Val Ile Pro Glu Trp Gln Ile Gln Arg Gly Lys Gln Val Phe
65                  70                  75                  80

His Leu Lys Gly Leu Met Thr Tyr Gly Ser Phe Trp Gly Asp Gly Gly
                85                  90                  95

Glu Arg Gly Pro Asp Phe Thr Ala Glu Ala Leu His His Thr Tyr Val
```

-continued

```
            100                 105                 110
Ser Met Ser Lys Phe Tyr Glu Asn Glu Ile Ala Lys Glu Arg Pro Val
            115                 120                 125
Thr Gln Ala Asp Arg Asp Met Ile Ser Val Arg Val Lys Arg Glu Ile
            130                 135                 140
His Glu Asn Gly Tyr Asp Ala Ala Ala Asn Ile Ile Arg Ile Asn Pro
145                 150                 155                 160
Ala Gln Val Phe Ala Tyr Gln Glu Leu Ile Thr His Tyr Thr Arg Met
                    165                 170                 175
Phe Thr Asp Ala Thr Tyr Glu Glu Ala Phe Met Lys Gly Arg Ile Glu
                    180                 185                 190
Asn His Ile Ser Ser Pro Glu Asp Leu Lys Ala Leu Ala Gly Tyr Phe
            195                 200                 205
Phe Trp Gly Gly Trp Val Ser Gly Ala Asn Arg Pro Gly Phe Asp Tyr
            210                 215                 220
Thr Tyr Thr His Asn Trp Pro Pro Asp Pro Leu Val Gly Asn Thr Pro
225                 230                 235                 240
Thr Phe Glu Thr Tyr Leu Trp Ser Phe Ile Ser Ile Phe Val Leu Phe
                    245                 250                 255
Cys Gly Thr Met Leu Val Leu Tyr Val Tyr Gly Glu Met Lys Val Leu
                    260                 265                 270
Pro Gly Glu Pro Phe Asn Gly Arg Asp Trp Ser Leu Thr Thr Val Asp
                    275                 280                 285
Leu Glu Asn Lys Gly Asp Ala Tyr Val Arg Pro Thr Gln Arg Ala Thr
            290                 295                 300
Tyr Lys Phe Phe Ala Phe Ala Val Ile Leu Phe Leu Val Gln Val Leu
305                 310                 315                 320
Ala Gly Ile Leu Ser Ala Glu Asp Phe Val Gly Gly Pro Gly Ser
                    325                 330                 335
Ala Ile Ala Thr Thr Val Leu Gly Phe Thr Ile Pro Phe Thr Val Thr
                    340                 345                 350
Arg Gly Trp His Thr Ile Val Gln Ile Tyr Trp Phe Phe Met Ala Trp
                    355                 360                 365
Val Gly Tyr Thr Leu Phe Phe Leu Pro Arg Ile Ser Lys Val Pro Asn
            370                 375                 380
Gly Gln Arg Phe Leu Ile Asn Leu Leu Phe Thr Leu Cys Leu Ile Val
385                 390                 395                 400
Gly Ala Gly Ala Leu Phe Gly Ile Tyr Leu Gly His Thr Gly Tyr Met
                    405                 410                 415
Thr Asp Asp Met Ala Tyr Trp Phe Gly Ser Gln Gly Trp Glu Phe Leu
                    420                 425                 430
Glu Leu Gly Arg Phe Trp His Ile Leu Met Leu Ala Ser Phe Cys Leu
            435                 440                 445
Trp Val Tyr Ile Ile Phe Arg Ala Val Lys Pro Trp Ile Thr Ser Gln
            450                 455                 460
Asn Leu Trp Ser Val Pro Ala Trp Leu Phe Tyr Gly Ser Gly Ile Met
465                 470                 475                 480
Val Leu Phe Leu Phe Gly Met Phe Met Thr Pro Ser Gln Asn Phe
                    485                 490                 495
Ala Ile Ala Asp Tyr Trp Arg Trp Met Asn Ile His Met Trp Val Glu
                    500                 505                 510
Val Thr Phe Glu Val Phe Thr Thr Cys Ile Val Gly Tyr Met Leu Val
            515                 520                 525
```

Gln Met Gly Leu Val Asn Arg Ala Met Ala Glu Arg Val Ile Phe Leu
         530                 535                 540
Ala Val Met Met Phe Leu Val Thr Ala Leu Ile Gly Ile Ser His Asn
545                 550                 555                 560
Phe Tyr Trp Ile Ala Lys Pro Thr Gly Ile Ile Ala Leu Gly Ser Val
             565                 570                 575
Phe Ser Thr Met Gln Val Leu Pro Leu Leu Ile Thr Leu Asp Ala
                 580                 585                 590
Trp Lys Met Arg Thr Glu Arg Thr Lys Ala His Glu Asn Ile Ala Glu
             595                 600                 605
Gly Lys Gln Arg Phe Val Met Asp Gly Val Trp Thr Phe Ile Leu Ala
             610                 615                 620
Val Asn Phe Trp Asn Ile Phe Gly Ala Gly Val Phe Gly Ser Leu Ile
625                 630                 635                 640
Asn Leu Pro Ile Val Asn Tyr Tyr Glu His Gly Thr Tyr Leu Thr Gly
                 645                 650                 655
Asn His Ala His Ala Ala Met Phe Gly Val Lys Gly Asn Ile Ala Ile
             660                 665                 670
Ala Gly Met Leu Phe Ala Cys Gln His Leu Phe Gln Arg Ser Ala Trp
             675                 680                 685
Asn Glu Lys Leu Ile Lys Gly Ile Phe Trp Ser Leu Gln Val Gly Leu
             690                 695                 700
Val Leu Met Met Met Leu Asp Leu Phe Pro Val Gly Leu Tyr Gln Val
705                 710                 715                 720
Ala Thr Val Phe Lys Glu Gly Leu Trp Ala Ala Arg Ala Gln Ala His
                 725                 730                 735
Val Thr Asp Ser Val Trp Ile Thr Leu Thr Trp Met Arg Thr Ile Gly
                 740                 745                 750
Gly Ala Val Phe Leu Phe Gly Gly Val Leu Pro Leu Val Tyr Phe Ile
             755                 760                 765
Leu Ser Arg Ala Gly Arg Met Val Arg Glu Ala Ser Val Val Glu Glu
             770                 775                 780
Gly Glu Trp Thr Ile Tyr Asp Arg Glu Lys Ala Lys Glu Arg Glu Ala
785                 790                 795                 800
Trp Ala Ala Gly Asp Glu Ala Phe
                 805

<210> SEQ ID NO 12
<211> LENGTH: 2427
<212> TYPE: DNA
<213> ORGANISM: Methylomirabilis oxyfera

<400> SEQUENCE: 12
atgagatcta gttcaagtag tggaatgggg aaaactaata ggaccttcgg ccaagccttg    60
ctgattaaga agtactggtg gcttcacgcc ttgatcgtga ccgttatcag tgtcattggg   120
ttggttgccc tcggtgtatg gacttatacc tcagctccgc cattgaccaa ttatgtcttg   180
tcatctaccg gagaaaccgt catccccgag tggcagatcc agcgcgggaa acaggtcttt   240
catctgaaag gtctgatgac ctatggctct ttttggggag acggcggtga acgcggtccg   300
gatttcaccg ctgaagcact acaccatacc tatgtatcaa tgagcaagtt ctacgaaaat   360
gagatcgcga aggagcgtcc cgtcacccag gcggatcgcg atatgatctc ggtcagggtc   420
aagcgcgaaa tccatgagaa cgggtatgat gcggctgcta acatcatccg tatcaatccg   480

```
gctcaggtct ttgcgtatca ggagttgatc acgcactata cgcgcatgtt tacggatgcc      540
acctacgaag aagcgttcat gaagggcagg atcgagaatc atatcagtag ccctgaagac      600
ctcaaagcac tagcgggata tttcttctgg ggaggttggg tctccggggc gaatcggccg      660
ggttttgact atacctacac tcacaactgg ccacccgatc cgctagtcgg taatactccg      720
acgttcgaga cctatctctg gagtttcatc tcgatcttcg tgctgttctg tggcaccatg      780
ctggtcctgt acgtctacgg ggagatgaag gtcctgcccg cgagccgtt caacgggcgc       840 gattggtcgc tcaccacggt cgaccttgaa aacaagggcg atgcctatgt gcggccgact      900
cagcgcgcca cctataagtt ctttgcgttc gctgtcatcc tgttcctggt gcaggtgctg      960
gccggtatcc tgagcgccga agatttcgtc ggcggtggac cgggtagtgc catcgccaca     1020
acggtattgg ggttcaccat ccccttcacc gttactcgcg ggtggcatac cattgtgcag     1080
atctactggt tcttcatggc ctgggtcggc tacactctct tcttcctgcc cgcatttcg      1140 aaggtgccga acggccagcg gttcctgatc aacctgctct ttacactatg tctgatcgtc     1200
ggcgcaggcg cgctgttcgg catctaccttt ggccacacgg ggtacatgac cgacgacatg     1260
gcctactggt tcggcagcca gggctgggag ttcctggagc tgggccgctt ctggcatatc     1320
ctgatgctgg cctcgttctg tctgtgggtc tacatcatct tccgcgctgt gaagccctgg     1380
atcaccagcc agaacctctg gtcagtgccg gcttggctgt tctacggcag cggtatcatg     1440
gtgctgttcc tgttcttcgg gatgttcatg accccatcgc agaacttcgc catcgccgac     1500
tactggcggt ggatgaacat tcacatgtgg gttgaggtca ccttcgaggt cttcaccacc     1560
tgtatcgttg ggtacatgct ggtgcagatg gtctggtca accgggcgat ggccgagcgg     1620
gttatcttcc tggccgtcat gatgttcctg gtaaccgccc tgatcgggat ctcccacaac     1680
ttctactgga tcgccaagcc gacagggatc atcgcactgg gcagcgtctt ctccaccatg     1740
caggtgctgc cgctgctgtt gatcaccctg gacgcctgga agatgcggac ggagcggacc     1800
aaggcccatg aaaacattgc cgagggtaag cagcgcttcg tgatggacgg cgtctggacg     1860
ttcattcttg ccgtcaactt ctggaacatc ttcggcgcgg gtgtcttcgg ctcgttgatc     1920
aacctgccca tcgtcaacta ctatgagcac ggcacctacc tcaccggcaa ccatgcccat     1980
gccgccatgt tcggtgtcaa gggtaacatc gccattgccg gtatgctgtt tgcctgccag     2040
cacctgttcc agcgctctgc ctggaatgag aagctgatca agggcatttt ctggtcgttg     2100
caggtcggct tggtgctgat gatgatgttg gacttgttcc ctgtcggtct gtaccaggtt     2160
gcaaccgtct tcaaggaagg cctttgggct gcccgagcac aggcgcacgt cacggatagt     2220
gtgtggatta ccttgacgtg gatgcgcacg atcggcggcg cggtcttcct gtttggcggc     2280
gtgttgcctc tcgtctattt cattctgtca agagcagggc ggatggtccg cgaagcctct     2340
gtcgtcgagg aaggtgaatg gaccatctac gacagggaga aggcgaagga gcgggaggct     2400
tgggcggccg gcgacgaggc attctaa                                         2427
```

<210> SEQ ID NO 13
<211> LENGTH: 810
<212> TYPE: PRT
<213> ORGANISM: Methylomirabilis oxyfera

<400> SEQUENCE: 13

Met Ser Pro Asn Pro Ser Gly Thr Ala Ala Lys Gly Lys Asn Glu Arg
1               5                   10                  15

Thr Phe Ala Gln Val Leu Leu Ile Lys Lys Tyr Trp Trp Leu His Ala
            20                  25                  30

```
Leu Ile Val Thr Ala Ile Ser Thr Ile Gly Leu Ile Ala Leu Gly Val
            35                  40                  45

Trp Thr Tyr Ala Gly Ala Pro Pro Leu Val Asn Phe Val Ser Lys Ser
        50                  55                  60

Gly Asp Val Val Ile Ala Glu His Ser Met Asn Arg Gly Lys Gln Val
 65                  70                  75                  80

Phe His Leu Lys Gly Leu Met Leu Tyr Gly Ser Phe Trp Gly Asp Gly
                85                  90                  95

Ala Glu Arg Gly Pro Asp Phe Thr Ala Glu Ala Leu His Arg Thr Phe
                100                 105                 110

Val Ser Met Gly Lys Tyr Tyr Glu Met Gln Ile Glu Lys Glu Gln Gly
            115                 120                 125

Arg Pro Ala Thr Gln Asp Glu Lys Asp Gly Ile Ala Gly Lys Val Lys
        130                 135                 140

Arg Glu Ile His Gln Asn Gly Tyr Asp Ala Ala Gly Val Ile Arg
145                 150                 155                 160

Leu Asn Asp Ala Gln Ile Phe Ala Tyr Asn Glu Leu Val Asp His Tyr
                165                 170                 175

Thr Lys Met Phe Thr Asp Pro Thr Tyr Glu Glu Ala Phe Gln Lys Gly
            180                 185                 190

Arg Ile Gln Ser Tyr Val Ser Asn Pro Glu Asp Ile Lys Gly Leu Ala
        195                 200                 205

Gly Tyr Phe Phe Trp Gly Gly Trp Val Ala Gly Ala Asn Arg Pro Gly
    210                 215                 220

Glu Ile Tyr Ser Tyr Thr His Asn Trp Pro Tyr Asp Pro Asp Ala Gly
225                 230                 235                 240

Asn Leu Pro Thr Tyr Ala Thr Tyr Ile Trp Ser Phe Leu Ser Ile Leu
                245                 250                 255

Val Leu Phe Ala Gly Thr Met Leu Val Leu Tyr Val Tyr Gly Glu Met
            260                 265                 270

Lys Ser Leu Pro Gly Glu Pro Phe Asn Gly Arg Asp Trp Ser Leu Thr
        275                 280                 285

Thr Val Asp Leu Glu Asn Lys Gly Asp Ala Tyr Val Arg Pro Thr Gln
    290                 295                 300

Arg Ala Thr Tyr Lys Phe Phe Ala Phe Ala Val Ile Leu Phe Leu Val
305                 310                 315                 320

Gln Val Leu Ala Gly Ile Leu Gly Ala Glu Asp Phe Val Gly Gly Gly
                325                 330                 335

Pro Gly Glu Ala Ile Leu Gly Ala Phe Gly Leu Val Ile Pro Phe Ser
                340                 345                 350

Val Val Arg Ser Tyr His Ala Ile Val Gln Ile Tyr Trp Phe Phe Met
            355                 360                 365

Ala Trp Val Gly Tyr Thr Leu Phe Leu Pro Arg Ile Ser Lys Val
        370                 375                 380

Pro Asn Gly Gln Arg Phe Leu Ile Asn Leu Leu Phe Ala Leu Cys Val
385                 390                 395                 400

Leu Val Gly Ala Gly Ala Leu Phe Gly Ile Tyr Ala Gly His Thr Gly
                405                 410                 415

Met Leu Thr Asp Asp Met Ala Tyr Trp Phe Gly Ser Gln Gly Trp Glu
            420                 425                 430

Phe Leu Glu Leu Gly Arg Phe Trp His Ile Leu Met Leu Ala Ser Phe
        435                 440                 445
```

```
Cys Leu Trp Val Tyr Ile Ile Phe Arg Ala Val Lys Pro Trp Ile Thr
450                 455                 460
Ser Gln Asn Leu Trp Ser Val Pro Ala Trp Leu Phe Tyr Gly Ser Gly
465                 470                 475                 480
Ile Met Val Leu Phe Leu Phe Phe Gly Met Phe Met Thr Pro Ser Gln
                485                 490                 495
Asn Phe Ala Ile Ser Asp Tyr Trp Arg Trp Met Asn Ile His Met Trp
            500                 505                 510
Val Glu Val Thr Phe Glu Val Phe Thr Thr Cys Ile Val Gly Tyr Met
        515                 520                 525
Leu Val Gln Met Gly Leu Val Asn Arg Ala Met Ala Glu Arg Val Ile
530                 535                 540
Phe Leu Ala Val Met Met Phe Leu Val Thr Ala Leu Ile Gly Ile Ser
545                 550                 555                 560
His Asn Phe Tyr Trp Ile Ala Lys Pro Thr Gly Ile Ile Ala Leu Gly
                565                 570                 575
Ser Val Phe Ser Thr Met Gln Val Leu Pro Leu Leu Leu Ile Thr Leu
            580                 585                 590
Asp Ala Trp Lys Met Arg Thr Glu Arg Thr Lys Ala His Glu His Leu
        595                 600                 605
Ser Glu Gly Lys Gln Arg Phe Val Met Asp Gly Val Trp Thr Phe Ile
610                 615                 620
Leu Ala Val Asn Phe Trp Asn Ile Phe Gly Ala Gly Val Met Gly Ser
625                 630                 635                 640
Leu Ile Asn Leu Pro Ile Val Asn Tyr Tyr Glu His Gly Thr Tyr Leu
                645                 650                 655
Thr Asn Asn His Ala His Gly Ala Met Phe Gly Val Lys Gly Asn Ile
            660                 665                 670
Ala Ile Ala Gly Met Leu Phe Ala Cys Gln His Leu Phe Gln Arg Ser
        675                 680                 685
Ala Trp Asn Glu Lys Leu Ile Lys Thr Val Phe Trp Ser Leu Gln Val
690                 695                 700
Gly Ile Val Met Met Met Leu Met Asp Met Phe Pro Val Gly Leu Tyr
705                 710                 715                 720
Gln Leu Ala His Ile Phe Gln Tyr Gly Phe Trp Tyr Gly Arg Gln Gln
                725                 730                 735
Ser Phe Val Thr Asn Glu Val Trp His Thr Leu Thr Trp Leu Arg Ser
            740                 745                 750
Ile Gly Gly Val Val Phe Leu Phe Gly Gly Val Leu Pro Leu Cys Trp
        755                 760                 765
Phe Ile Leu Ser Arg Ala Gly Arg Met Val Arg Glu Ala Ala Val Val
770                 775                 780
Glu Glu Gly Glu Trp Thr Ile Tyr Asp Arg Glu Lys Ala Lys Glu Arg
785                 790                 795                 800
Glu Ala Trp Ala Ala Ser Asp Glu Ala Phe
                805                 810
```

<210> SEQ ID NO 14
<211> LENGTH: 2433
<212> TYPE: DNA
<213> ORGANISM: Methylomirabilis oxyfera

<400> SEQUENCE: 14
atgagtccga atcccagcgg aactgcagca aagggcaaga acgagaggac atttgcacaa    60

-continued

```
gtactactta tcaagaagta ttggtggctt catgctttga tcgttaccgc gattagcacc      120
atcggtttga ttgctctcgg cgtctggacc tacgcgggcg ctcccctct ggttaacttc       180 gtaagcaaat caggggacgt ggtcattgct gagcattcca tgaatcgtgg aaagcaggtg      240
tttcacctga agggtctgat gctctacgga tccttctggg gtgacggcgc agagcgcgga     300
ccggatttca ccgcagaagc tctgcatcga accttcgtct ccatgggcaa gtactatgag     360
atgcagattg agaaagagca gggccgcccc gcaacccagg acgagaagga cgggatcgcg    420
ggaaaggtca gcgagagat tcatcagaac ggttatgacg cagcagcagg cgtcatccgc     480
ctgaacgatg cccagatctt tgcgtataat gaattggtcg accattacac caagatgttc    540
accgatccca cctatgaaga ggcattccag aagggtcgga ttcagagcta tgtcagcaac    600
ccggaggaca tcaagggatt ggcgggttac ttcttctggg gcggctgggt agccggcgca    660
aatcgaccgg gcgagatcta cagctatacc cacaactggc cgtatgatcc tgatgccggc   720
aacctcccga cgtacgcgac gtacatctgg agcttcctct cgatcctcgt gctgttcgct   780
ggcaccatgc tggtcctgta cgtctatggc gaaatgaagt ccctgcccgg cgagccgttc   840
aacgggcgcg attggtcgct caccacggtc gaccttgaaa acaagggcga tgcctatgtg   900
cggccgactc agcgcgccac ctataagttc tttgcgttcg ctgtcatcct gttcctggtg   960
caggtgctgg ccggtatcct gggcgccgag gatttcgtcg gcggtggacc gggtgaagcg   1020
atcttgggcg cgttcggact cgtcatcccc ttcagcgtcg tccgaagcta tcatgccatc    1080
gtccagatct actggttctt catggcctgg gttggctaca ccttttctt cctgccccgc     1140 atttcgaagg tacccaacgg gcagcggttc ctgatcaacc tactctttgc gctgtgcgtg   1200
ctcgttggcg ccggtgcgct gttcgggatt tatgccggcc acactggtat gctgaccgac   1260
gacatggcct actggttcgg cagccagggc tgggagttcc tggagctggg ccgcttctgg  1320
catatcctga tgctggcctc gttctgtctg tgggtctaca tcatcttccg cgctgtgaag  1380
ccctggatca ccagccagaa cctctggtca gtgccggctt ggctgttcta cggcagcggt   1440
atcatggtgc tgttcctgtt cttcgggatg ttcatgaccc catcgcagaa cttcgccatc   1500
tccgactact ggcggtggat gaacattcac atgtgggttg aggtcacctt cgaggtcttc   1560
accacctgta tcgttgggta catgctggtg cagatgggtc tggtcaaccg ggcgatggcc   1620
gagcgggtta tcttcctggc cgtcatgatg ttcctggtaa ccgccctgat cgggatctcc   1680
cacaacttct actggatcgc caagccgaca gggatcatcg cactgggcag cgtcttctcc   1740
accatgcagg tgctgccgct gctgttgatc accctggacg cctggaagat gcggacggag  1800
cggaccaagg cccatgagca ccttctgag ggcaagcagc gcttcgtgat ggacggtgtc     1860
tggacgttca tcctcgccgt caacttctgg aacatcttcg gtgccggtgt catgggctcg     1920
ttgatcaacc tgcccatcgt caactactat gagcacggca cctacctcac caacaaccat    1980
gcccatggcg ccatgttcgg tgtcaagggt aacatcgcca ttgccggtat gctgtttgcc     2040
tgccagcacc tgttccagcg ctctgcctgg aatgagaagc tgatcaagac tgtcttttgg    2100
tccctgcagg tcggcatcgt gatgatgatg ctcatggata tgttcccggt cggtctgtat     2160
cagctcgccc acatcttcca gtatgggttc tggtatggcc gccagcagtc gttcgtcacc    2220
aacgaggtat ggcacacgct gacttggctt cggtcaatcg gcggcgtggt cttcctgttc    2280
ggtggtgttc tgcctctgtg ctggttcatt ctgtcgaggg ctggacggat ggtccgcgaa   2340
gctgccgtcg ttgaagaggg cgagtggacg atctacgaca gagagaaggc gaaagagcga   2400
gaggcttggg ccgcttctga cgaggcgttc tag                                 2433
```

<210> SEQ ID NO 15
<211> LENGTH: 476
<212> TYPE: PRT
<213> ORGANISM: Moorella thermoacetica

<400> SEQUENCE: 15

```
Met Asp Tyr Lys Pro Val Lys Thr Phe Ser Glu Leu Glu Val Lys Ser
1               5                   10                  15

Leu Asp Asp Phe Val Tyr Gly Ile Ala Pro His Pro Val Lys Ala Lys
            20                  25                  30

Asn Gly Met Val Ile Gly Ala Gly Thr Val Tyr Pro Glu Ile Asn Met
        35                  40                  45

Thr Leu Pro Pro Met Asn Ile Glu Glu Ser Thr Met Pro Glu Val Arg
    50                  55                  60

Arg Gln Tyr Ala Glu Met Ile Glu Gly Ile Leu Lys Arg Ala Arg Asp
65                  70                  75                  80

Leu Tyr Ala Pro Gly Ile Ile Val Glu Leu Glu Leu Pro Glu Thr
            85                  90                  95

Thr Met Lys Pro Glu Trp Gly Ile Glu Ile Asn Lys Ile Leu Arg Asp
            100                 105                 110

Lys Met His Glu Tyr Glu Asp Lys Tyr Gly Leu Lys Ser Leu Leu Arg
        115                 120                 125

Cys Thr Pro Asn Asp Thr Arg Glu Ile Leu Arg Pro Pro Leu Met Lys
    130                 135                 140

Arg Gly Glu Leu Leu Glu Asn Met Phe Ile Thr Phe Glu Lys Cys Ala
145                 150                 155                 160

Glu Asp Gly Ala Asp Ile Leu Ser Ile Glu Ser Thr Gly Gly Lys Glu
                165                 170                 175

Val His Asp Glu Ala Leu Val Thr Cys Asn Ile Arg Lys Ala Ile Phe
            180                 185                 190

Ala Leu Gly Val Leu Gly Val Arg Asp Met Arg Phe Leu Trp Ser Asn
            195                 200                 205

Ile Val Arg Ile Ala Glu Arg Thr Gly Ala Ile Ala Gly Gly Asp Thr
    210                 215                 220

Ala Cys Gly Phe Ala Asn Thr Ala Leu Ala Leu Ala Glu Gln Gly Met
225                 230                 235                 240

Ile Pro Arg Val Phe Ala Ala Val Asp Arg Val Ala Thr Ile Pro Arg
                245                 250                 255

Ser Leu Val Ala Phe Glu Met Gly Ala Ile Gly Pro Asp Lys Asp Cys
            260                 265                 270

Gly Tyr Glu Gly Pro Tyr Met Lys Ala Ile Ala Gly Val Pro Ile Ser
        275                 280                 285

Met Glu Gly Lys Thr Ala Ala Cys Ala His Leu Ser Ala Ile Gly Asn
    290                 295                 300

Ile Ala Ala Cys Val Cys Asp Met Trp Ser Asn Glu Ser Val Gln Asn
305                 310                 315                 320

Val Lys Leu Leu Ser Ala Pro Ala Pro Val Val Ser Thr Glu Gln Leu
                325                 330                 335

Ile Tyr Asp Cys Arg Leu Met Asn Glu Ala Ala Asp Gly Arg Ser
            340                 345                 350

Phe Ala Leu Lys Met Arg Asp Trp Leu Ala Ala Ser Asp Ser Arg Leu
        355                 360                 365

Asp Pro Gln Ala Tyr Val Leu Arg Pro Asp Ile Val Leu Glu Ile Ser
```

```
                370           375           380
Gln Glu Leu Val Lys Glu Lys Asp Ala Phe Ile Ala Thr Lys Ala
385                 390                 395                 400

Ala Ala Leu Ala Ala Glu Val Ile Lys Arg Gly Leu Ala Arg Gly Glu
                405                 410                 415

Val Gln Val Ser Ser Arg Glu Lys Lys Trp Leu Asp Ile Ile Ser Ser
                420                 425                 430

Gln Ile Glu Thr Ile Pro Asp Asp Trp Glu Gln Phe Trp Tyr Glu Ile
                435                 440                 445

Gln Lys Glu Leu Asp Leu Glu Lys Phe Arg Pro Glu Glu Tyr Asp Leu
450                 455                 460

Glu Val Ile Met Ala Arg Gly Ala Ser Ala Gly Asn
465                 470                 475

<210> SEQ ID NO 16
<211> LENGTH: 1431
<212> TYPE: DNA
<213> ORGANISM: Moorella thermoacetica

<400> SEQUENCE: 16
atggattaca agcctgttaa aacctttagt gaactggagg tcaaatccct ggatgatttc      60
gtctacggga ttgcgcccca tcccgtaaaa gcaagaacg gcatggtgat cggcgcaggg     120
acggtttacc ccgagatcaa catgaccctc ccgccgatga atattgagga agcaccatg     180 cccgaagtca gaaggcagta tgcggagatg attgagggga ttttaaagag ggcgagggac     240
ctgtacgccc ccgcatcat cgtggaactg gaactgctcc ggagactac catgaagccc     300 gagtgggga tcgagattaa caagatcctg cgggacaaga tgcacgagta cgaggataag     360
tacgggctaa aaagcctcct caggtgtacc cccaacgaca ccaggagat tctcaggccg     420 ccgctgatga acggggcga actcctggaa acatgttca tcacctttga gaaatgcgcc     480
gaggacgggg ctgatatcct ttccatcgag tccacgggcg gtaaggaggt ccacgatgaa     540
gcgcttgtca cctgcaacat caggaaggcc atctttgccc tgggtgtcct gggggtcagg     600
gacatgcggt tcctctggtc caatatagtc aggatcgccg aacggaccgg cgctatagcc     660
ggtggagata cggcatgcgg gtttgctaac accgccctcg ccctggcgga cagggaatg     720 atccccaggg tgtttgcggc agtggacagg gtggccacca tccccaggag cctggtggca     780
ttcgaaatgg gtgccatagg gcctgataag gactgcggct atgagggggcc atacatgaaa     840 gccatcgccg gggtacccat ttccatgaaa ggcaaaacgg cggcatgtgc ccatttaagt     900
gccatcggca acatcgccgc ctgtgtgtgc gacatgtgga gcaacgaatc cgtccagaac     960
gtcaagctgc tgagcgctcc ggcacccgtg gtatccacgg aacagctcat ctacgactgc    1020
cggctgatga acgaagcggc ggcggacggg cgcagcttcg ccctgaagat gcgggactgg    1080
ctggcagcct ccgattccag gctggatccc caggcctacg tcctgaggcc ggacatagtg    1140
ctggagatca gccaggaatt ggttaaggaa aaggacgctt tcattgcgac caaaaaggcg    1200
gccgccctgg cggcggaggt cattaagcgg ggcctggccc ggggcgaagt tcaggtgtcc    1260
tccagagaga agaagtggtt ggacatcatc agctcccaga ttgaaacaat acccgacgat    1320
tgggaagagt tctggtacga aatacaaaaa gaactggacc tcgaaaaatt taggccggag    1380
gaatatgatt tagaggtaat catggccaga ggagcttccg cagggaatta g            1431

<210> SEQ ID NO 17
<211> LENGTH: 349
```

<212> TYPE: PRT
<213> ORGANISM: Moorella thermoacetica

<400> SEQUENCE: 17

```
Met Leu Lys Gln Arg Glu Trp Met Thr Pro Lys Arg Phe Leu Ser
1               5                   10                  15

Ala Leu Phe Gly Gly Arg Val Asp Arg Thr Pro Val Ala Asn Pro Thr
                20                  25                  30

Ser Leu Val Thr Val Glu Leu Met Glu Arg Thr Gly Ala Tyr Phe Pro
            35                  40                  45

Asp Ala His Leu Asp Ala Glu Lys Met Ala Arg Leu Ala Ala Thr Ser
        50                  55                  60

Tyr Glu Val Leu Gly Phe Asp Thr Ile Met Pro Val Phe Ser Ala His
65                  70                  75                  80

Thr Glu Ser Ala Ala Leu Gly Val Pro Val Asp Trp Gly Asp Lys Met
                85                  90                  95

Ser Trp Pro Val Asn Thr Ser His Pro Ile Thr Asp Pro Glu Gln Ile
                100                 105                 110

Val Ile Pro Asp Ser Phe Leu Glu Glu Pro Ser Met Arg Thr Val Leu
            115                 120                 125

Asp Ala Ile Lys Ile Leu Arg Ser Gln Tyr Gly Asp Arg Val Ala Ile
        130                 135                 140

Ile Gly Lys Thr Tyr Gly Pro Trp Ser Leu Ala Tyr His Leu Val Gly
145                 150                 155                 160

Thr Glu Asn Phe Leu Met Glu Thr Ile Leu Asn Pro Asp Lys Ala Arg
                165                 170                 175

Arg Tyr Leu Glu Val Leu Leu Glu Ala Ser Leu Leu Ser Ala Lys Ala
                180                 185                 190

Gln Ile Lys Ala Gly Ala Asp Ala Ile Leu Trp Gly Asp His Ala Thr
            195                 200                 205

Gly Asp Leu Val Ser Ala Glu Tyr Tyr Arg Asp Phe Leu Met Lys Val
        210                 215                 220

His Gln Tyr Val Thr Arg Glu Val Gly Ala Pro Ile Ile Leu His Ile
225                 230                 235                 240

Cys Gly Asn Thr Thr Lys Phe Ile Pro Tyr Ile Val Glu Ala Gly Phe
                245                 250                 255

Asp Ala Phe His Phe Asp Ser Lys Val Asp Ala Lys Leu Ala Lys Glu
                260                 265                 270

Leu Ala Gly Asn Lys Met Ser Leu Ile Gly Asn Ile Asn Asn Pro Val
            275                 280                 285

Thr Leu Leu Ala Gly Thr Pro Glu Asp Val Lys Lys Glu Thr Leu Tyr
        290                 295                 300

Ala Ile Glu Ala Gly Val Glu Ile Val Gly Pro Glu Cys Ala Ile Pro
305                 310                 315                 320

Leu Thr Thr Pro Leu Glu Asn Ile Leu Ala Ile Thr Glu Thr Ala Lys
                325                 330                 335

Glu Tyr Gln Ile His Lys Lys Leu Gly Gly Glu Thr Gln
                340                 345
```

<210> SEQ ID NO 18
<211> LENGTH: 1050
<212> TYPE: DNA
<213> ORGANISM: Moorella thermoacetica

<400> SEQUENCE: 18

```
atgttaaagc aacgagaatg gatgacaccg aaaaggcgct tcctatctgc gcttttcggt    60
ggaagagttg atcgtacacc ggtagcgaat cccacatctt tggtgacagt agaattaatg   120
gagcgaaccg gtgcttattt tccagatgcc catttagatg cggaaaaaat ggctagattg   180
gcggctacaa gttacgaggt attaggattt gatactatta tgccagtgtt tagtgcccat   240
acagaatcag ccgccttagg agtacctgtc gattggggag ataagatgag ttggcctgta   300
aatacttctc acccaattac tgatccggag cagatagtta taccagatag ctttctagag   360
gagccatcaa tgcgtactgt tttggatgcc ataaagattc taaggagtca gtatggagat   420
agggtggcaa ttatcggcaa gacatatggc ccatggtctc tagcctatca tctggtagga   480
acggaaaatt ttttaatgga aacaattcta aatccggaca aggcaagaag atacctcgaa   540
gtattattgg aagcctcttt gctttccgcc aaggcacaaa ttaaggctgg tgcagatgct   600
attttatggg gggaccacgc tactggtgat ctggtaagcg cagaatatta tcgggatttt   660
cttatgaaag ttcatcagta tgtgactagg gaagtcggag ctcctattat cctgcatatt   720
tgtgggaata ctaccaaatt cattccttat attgtagaag ccggatttga tgcttttcat   780
tttgattcta aagtcgatgc caaactagct aaagaattgg ctggaaataa gatgtcttta   840
attggaaaca tcaataatcc tgtaacattg ctcgccggca cacctgaaga tgttaaaaaa   900
gagactctat acgcaattga ggctggcgtg gaaatagtcg cccagaatg tgctattcct   960
ttgacaacgc cccttgaaaa catttttagct attactgaaa ccgcaaaaga atatcaaatt  1020
cataaaaaac taggaggga gacacaatga                                      1050
```

<210> SEQ ID NO 19
<211> LENGTH: 350
<212> TYPE: PRT
<213> ORGANISM: Moorella thermoacetica

<400> SEQUENCE: 19

Met Ser Ala Ser Glu Gln Met Ala Gly Ser Glu Arg Val Ile Ala Ala
1               5                   10                  15

Val Gln Gly Gln Glu Val Asp Arg Phe Pro Leu Val Thr Pro Thr Ser
                20                  25                  30

Val Val Thr Val Glu Ser Met Thr Val Thr Gly Val Tyr Phe Pro Glu
            35                  40                  45

Ala His Thr Asp Pro Tyr Lys Met Ala Ala Leu Ala Ala Ala Gly His
        50                  55                  60

Glu Leu Leu Gly Phe Asp Thr Val Thr Pro Tyr Phe Ser Ile Leu Leu
65                  70                  75                  80

Glu Ala Ala Ala Leu Gly Cys Glu Val Asp Leu Asn Ser Val Asp Ala
                85                  90                  95

Met Pro Ala Ile Lys Ile Asn Pro Leu Lys Asn Leu Leu Glu Arg Lys
            100                 105                 110

Trp Asp Trp Arg Pro Pro Ala Asn Phe Leu Asp Arg Gln Pro Val Lys
        115                 120                 125

Ala Leu Leu Ala Ala Ile Arg Leu Leu Lys Lys Arg Tyr Gly Arg Arg
    130                 135                 140

Val Ala Val Val Gly Lys Val Ile Gly Pro Trp Thr Leu Ala Tyr His
145                 150                 155                 160

Leu Cys Gly Val Gln Asp Phe Leu Leu Gly Leu Val Leu Glu Pro Glu
                165                 170                 175

Ala Val Arg Glu Leu Leu Glu Arg Leu Leu Ala Val Pro Leu Arg Leu
            180                 185                 190

```
Ala Val Ala Glu Ile Glu Ala Gly Val Asp Val Leu Thr Trp Ala Asp
        195                 200                 205

His Ala Thr Ser Asp Leu Val Ser Ala Ala Ala Tyr Arg Asp Phe Leu
    210                 215                 220

Leu Pro Leu His Gln Arg Ala Met Glu Gln Leu Ala Gly Ser Cys Pro
225                 230                 235                 240

Val Ile Leu His Thr Cys Gly Arg Ala Thr Asp Arg Val Ala Tyr Phe
                245                 250                 255

Ala Arg Ala Gly Phe Thr Ala Phe His Phe Asp Ser Arg Asn Pro Val
                260                 265                 270

Gly Asp Leu Leu Ser Leu Ala Asn Gly Arg Leu Asn Leu Ile Gly Gly
                275                 280                 285

Ile Asn Asn Pro Gln Thr Leu Leu Asn Gly Lys Val Lys Glu Val Arg
290                 295                 300

Ala Thr Ile Glu Gly Leu Leu Gln Ala Gly Ile Lys Met Val Ala Pro
305                 310                 315                 320

Glu Cys Ala Val Pro Leu Arg Thr Pro Asn Gln Asn Leu Arg Ala Ile
                325                 330                 335

Val Gln Ala Val Arg Asp Phe Ser Arg Arg His Arg Lys Val
                340                 345                 350

<210> SEQ ID NO 20
<211> LENGTH: 1053
<212> TYPE: DNA
<213> ORGANISM: Moorella thermoacetica

<400> SEQUENCE: 20
gtgtccgcca gcgagcaaat ggcaggtagt gagagggtga tagcagccgt gcaggggcag      60
gaggttgacc gcttcccct ggttacgccg acctcggtgg tgacggtaga aagcatgacc      120
gtcaccggtg tttatttccc ggaggccac accgacccct ataaaatggc cgccctggct      180
gcggccggcc acgaattact gggctttgat accgtcaccc cttatttcag catcctgctt      240
gaggcggcgg cccttgggtg cgaagtggac ttgaactcgg tggacgccat gccagccatt      300
aaaattaacc ctctgaagaa ccttttggag aggaagtggg actggcgccc gcctgccaat      360
ttcctggatc ggcaaccggt aaaagccctc ctggctgcta tcagactatt aaaaaagcgc      420
tatggcaggc gcgtggccgt ggtgggtaag gtgatcggcc cctggaccct ggcttaccat      480
ctgtgcgggg ttcaggactt cctcctaggg ctggttctgg aaccggaagc cgtccgggaa      540
ctcttagagc ggttgctggc cgttcctttg cgtctggcag tagctgagat tgaagccggg      600
gttgatgtcc tcacctgggc tgatcacgct accagcgacc tggtcagcgc tgctgcttac      660
cgggattttc tcctgcctct ccaccagagg gctatggagc aattagccgg tagttgtccg      720
gtgattttgc atacctgtgg ccgggctacc gaccgggtgg cttatttcgc ccgggctggg      780
tttaccgcct tcattttga ctcccgcaac cggtcggcg atcttctgtc cctgccaat      840 ggccggttga atctcatcgg tggcatcaac aaccccaga ccttgctgaa cggtaaagtg      900
aaggaagtta gagcaaccat cgaaggcctg ttacaggcgg gtatcaagat ggtagccccg      960
gaatgcgccg tgcccctgcg gacacccaac cagaacctcc gggccatagt tcaggcggtg     1020
cgcgacttca gccgccgcca ccggaaggtt tga                                 1053

<210> SEQ ID NO 21
<211> LENGTH: 464
<212> TYPE: PRT
```

<213> ORGANISM: Acetobacterium woodii

<400> SEQUENCE: 21

```
Met Glu Asp Lys Met Lys Lys Thr Phe Asn Lys Leu Ala Ile Ser Lys
1               5                   10                  15

Leu Asp Asp Phe Val Tyr Gly Ser Cys Pro Asn Pro Val Thr Thr Lys
            20                  25                  30

Ser Gly Met Val Ile Gly Gly Leu Val Tyr Pro Glu Leu Asn Phe
        35                  40                  45

Thr Leu Pro Gly Met Asp Val Asn Asp Ala Thr Met Asp Lys Ala Ala
    50                  55                  60

Arg Ile Tyr Thr Asp Ile Ile Thr Thr Ser Leu Gln Arg Ala Ala Glu
65                  70                  75                  80

Leu Lys Ser Pro Gly Val Leu Ile Glu Phe Glu Thr Ile Pro Asp Phe
                85                  90                  95

Thr Glu Val Pro Ala Tyr Gly Arg Arg Ile Asn Gln Ile Leu Ile Asp
            100                 105                 110

Glu Ile Lys Ala Ala Asp Lys Tyr Gly Leu Lys Ala Thr Leu Arg
        115                 120                 125

Thr Thr Pro Asn Asp Leu Arg Glu Met Ser Arg Pro Pro Val Met Arg
    130                 135                 140

Gly Gly Lys Tyr Trp Asp Thr Met Leu Glu Leu Phe Asn Asn Cys Ala
145                 150                 155                 160

Lys Asp Gly Thr Asp Phe Leu Ser Ile Glu Ser Thr Gly Gly Lys Glu
                165                 170                 175

Ile His Asp Asp Ala Leu Val Lys Ala Asp Ile Arg Lys Ser Ile Leu
            180                 185                 190

Ala Met Gly Val Leu Gly Cys Ile Asp Met Glu Phe Leu Trp Ala Glu
        195                 200                 205

Ile Val Lys Ile Cys Asp Ala His Asp Cys Leu Pro Ala Gly Asp Ser
    210                 215                 220

Ala Cys Gly Phe Ala Asn Thr Ala Met Val Leu Ala Glu Lys Gly Phe
225                 230                 235                 240

Ile Pro Arg Ser Phe Ala Ala Val Val Arg Val Val Ala Val Pro Arg
                245                 250                 255

Ser Leu Val Ala Phe Glu Gln Gly Cys Val Gly Pro Asp Lys Asp Cys
            260                 265                 270

Ala Tyr Glu Gly Pro Tyr Leu Lys Ala Ile Thr Gly Cys Pro Ile Ser
        275                 280                 285

Met Glu Gly Lys Thr Ala Ala Pro Ala His Met Ser Pro Val Gly Asn
    290                 295                 300

Val Ala Ala Cys Val Cys Asp Val Trp Ser Asn Glu Ser Ile Gln Gln
305                 310                 315                 320

Val Leu Leu Leu Ser Gly Met Ala Pro Val Val Gly Met Glu Gln Leu
                325                 330                 335

Ile Tyr Asp Cys Arg Leu Met Asn Ala Ala Thr Ala Lys Gly Gln Gln
            340                 345                 350

Phe Met Met Arg Asp Leu Leu Ser Asp Ser Asp Ala Ser Leu Asp Pro
        355                 360                 365

Gln Ala Tyr Val Leu Ser Pro Glu Val Val Leu Arg Ile Ser Ala Glu
    370                 375                 380

Ile Val Lys Ala Thr Pro Asp Gly His Leu Ala Met Thr Ile Ala Ala
385                 390                 395                 400
```

```
Ala Arg Gly Ala Ile Glu Glu Ile Lys Ala Gly Ile Thr Ser Gly Lys
            405                 410                 415

Val Gln Ala Asp Lys Arg Asp Met Lys Trp Leu Asp Lys Met Ser Arg
        420                 425                 430

Gln Ile Asp Thr Ile Pro Asn Asp Pro His Glu Phe Tyr Lys Met Met
        435                 440                 445

Glu Pro Glu Leu Asp Leu Thr Thr Phe Thr Ala Ser Glu Tyr Gly Leu
    450                 455                 460
```

<210> SEQ ID NO 22
<211> LENGTH: 1395
<212> TYPE: DNA
<213> ORGANISM: Acetobacterium woodii

<400> SEQUENCE: 22

| | | | | | |
|---|---|---|---|---|---|
| atggaggata | aaatgaaaaa | aacgttcaat | aaattagcga | ttagcaagtt | agacgatttt | 60 |
| gtgtatggaa | gctgtccaaa | tcctgttaca | accaaaagtg | ggatggtaat | tggcggcgga | 120 |
| ttagtttatc | cggaacttaa | ctttacgctt | ccaggcatga | tgtaaacga | tgcaacaatg | 180 |
| gataaagccg | ccagaattta | taccgatatt | atcacgacgt | cattacaacg | agcggcagaa | 240 |
| ttaaaatcac | ctggcgtttt | gatcgaattt | gaaaccattc | ccgatttcac | ggaagttcct | 300 |
| gcttatggtc | gaagaattaa | tcagatcttg | atcgatgaaa | taaaagccgc | ggctgataaa | 360 |
| tatggattaa | aagcaacact | tcgaacaacc | caaatgact | tacgagaaat | gagtcgtcca | 420 |
| ccagtaatgc | gaggcggaaa | atattgggat | acgatgttgg | agcttttaa | taattgcgct | 480 |
| aaagatggta | ccgactttt | atcaattgaa | tctaccggtg | caaagaaat | tcatgatgat | 540 |
| gcgctagtga | aagcagatat | cagaaaatca | atcctggcga | tgggagttct | tggatgtatt | 600 |
| gatatggaat | tttatgggc | cgaaattgta | aaaatttgtg | atgcccatga | ttgcttgcca | 660 |
| gctggcgatt | cagcgtgtgg | atttgccaat | acggccatgg | ttttagcaga | aaaggatt | 720 |
| attcccgtt | cttttgcggc | agtcgttcgg | gttgtggcag | tgccgagatc | attagttgct | 780 |
| tttgaacaag | ggtgtgtcgg | tcctgataaa | gattgcgcct | atgaaggtcc | ttatttgaaa | 840 |
| gcgatcactg | gttgcccaat | tcaatgaa | ggtaaaacag | cagctccggc | tcatatgagc | 900 |
| cccgttggaa | atgtggctgc | atgcgtttgt | gatgtctgga | gtaatgaatc | aatccaacaa | 960 |
| gtgttgttat | tatcagggat | ggcgccagtt | gtcgggatgg | aacaactat | ttatgactgt | 1020 |
| cgtttaatga | atgcggcaac | cgctaaaggg | caacaattca | tgatgcgtga | tttattatcg | 1080 |
| gattctgatg | catcattgga | tccacaggct | tatgtactaa | gtccggaagt | tgtttaaga | 1140 |
| atcagtgctg | aaattgttaa | agcgactccc | gatgggcatt | tagccatgac | aattgcggca | 1200 |
| gcgcgaggag | cgattgaaga | aataaaagcc | gggattacca | gcggtaaagt | acaagctgat | 1260 |
| aaacgtgata | tgaaatggct | ggataaaatg | tcgcgacaaa | ttgataccat | tccaaatgat | 1320 |
| ccgcacgaat | tctacaagat | gatggaacca | gaattagatt | taacaacatt | tacggccagt | 1380 |
| gaatatggtc | tataa | | | | | 1395 |

<210> SEQ ID NO 23
<211> LENGTH: 460
<212> TYPE: PRT
<213> ORGANISM: Eubacterium limosum

<400> SEQUENCE: 23

```
Met Ala Lys Lys Phe Asp Lys Leu Ala Ile Asn Asn Leu Asp Asp Phe
1               5                   10                  15
```

-continued

```
Ile Tyr Gly Ser Cys Pro Asn Pro Val Thr Thr Arg Ser Gly Met Val
             20                  25                  30
Ile Gly Gly Gly Thr Ile Tyr Pro Glu Ile Asn Phe Thr Leu Pro Gly
         35                  40                  45
Met Asp Val Asn Asp Gln Thr Ile Asp Lys Ala Leu Gly Ile Tyr Ser
 50                  55                  60
Asn Ile Ile Asp Gly Val Leu Lys Arg Ala Ala Glu Leu Tyr Ala Pro
 65                  70                  75                  80
Gly Val Leu Val Glu Phe Glu Thr Val Pro Asp Phe Thr Glu His Pro
                 85                  90                  95
Lys Tyr Gly Ile Asp Ala Asn Arg Ile Leu Leu Asn Gly Ile Lys Glu
            100                 105                 110
Ala Ala Asp Lys Tyr Gly Leu Lys Ala Ala Leu Arg Thr Thr Pro Asn
            115                 120                 125
Asp Leu Arg Glu Met Ser Arg Pro Pro Val Met Arg Gly Gly Lys Tyr
130                 135                 140
Trp Asp Thr Met Leu Glu Leu Tyr Glu Gln Cys Ala Lys Asp Gly Ser
145                 150                 155                 160
Asp Phe Leu Ser Ile Glu Ser Thr Gly Gly Lys Glu Ile Asn Asp Glu
                165                 170                 175
Ala Leu Val Lys Ala Asp Ile Arg Lys Ala Ile Phe Ala Met Gly Val
            180                 185                 190
Leu Gly Cys Arg Asp Met Glu Tyr Leu Trp Gly Asn Leu Val Lys Leu
            195                 200                 205
Ser Asp Ala Asn Gly Cys Phe Ala Ala Gly Asp Ser Ala Cys Gly Phe
210                 215                 220
Ala Asn Thr Ala Met Val Leu Ala Glu Lys Gly Phe Ile Pro His Val
225                 230                 235                 240
Phe Ala Ala Val Met Arg Val Val Ala Val Pro Arg Ala Leu Val Ala
                245                 250                 255
Phe Glu Gln Gly Ala Val Gly Pro Ser Lys Asp Cys Ala Tyr Glu Gly
            260                 265                 270
Pro Tyr Leu Lys Ala Ile Thr Gly Ser Pro Ile Ala Met Glu Gly Lys
            275                 280                 285
Ser Ala Ala Gly Ala His Leu Ser Pro Val Gly Asn Ile Ala Ala Ala
290                 295                 300
Val Ala Asp Thr Trp Ser Asn Glu Ser Ile Gln Gln Val Lys Leu Leu
305                 310                 315                 320
Ser Glu Met Ala Pro Val Val Gly Met Glu Gln Leu Val Tyr Asp Cys
                325                 330                 335
Arg Leu Met Asn Val Ala Lys Glu Lys Gly Gln Gly Leu Met Met Arg
            340                 345                 350
Asp Leu Leu Val Glu Ser Asp Ala Pro Leu Asp Val Gln Ala Trp Val
            355                 360                 365
Leu Arg Pro Asp Val Val Leu Lys Ile Ala Gly Glu Leu Val Lys Glu
            370                 375                 380
Gln Asp Asn Phe Leu Arg Thr Lys Leu Ala Ala Lys Leu Thr Ile Asn
385                 390                 395                 400
Glu Leu Arg Asp Ala Ile Lys Ala Glu Lys Val Lys Ala Asp Arg Arg
                405                 410                 415
Asp Met Lys Trp Leu Asp Lys Met Glu Lys Ala Val Asp Lys Ile Pro
            420                 425                 430
Asp Asp Pro Glu Gln Phe Tyr Ala Glu Ile Lys Pro Glu Leu Asp Met
```

```
                    435                 440                 445

Asp Lys Trp His Pro Lys Gly Tyr Gly Leu Lys Ala
    450                 455                 460

<210> SEQ ID NO 24
<211> LENGTH: 1383
<212> TYPE: DNA
<213> ORGANISM: Eubacterium limosum

<400> SEQUENCE: 24
atggcaaaga aatttgataa actggcaatt aataatctgg acgattttat ttatggctct     60
tgtccgaacc ctgtcaccac caggagcggc atggtcatcg gcggcggcac catctatccg    120
gaaatcaact tcacactgcc gggcatggat gtcaatgatc agaccattga caaggccttg    180
ggcatttatt ccaatatcat cgacggtgtg ctcaagagag cggcagagct ctacgcgccc    240
ggcgtgctgg tagaatttga aaccgtgccg gactttaccg agcatccaaa atatgggatt    300
gacgccaacc gcatttttat taaatggcat caaggaagcc gcagacaagta cggcctcaag    360 gccgccctgc ggaccacccc caacgacctg cgcgaaatga ccgtcctcc ggttatgcgc     420 ggcggcaagt actgggatac catgctggag ctgtacgaac agtgcgccaa ggatggttca    480 gacttttat ccatcgaatc gaccggggc aaggaaatca tgacgaagc cctcgtaaag       540 gccgatatcc gcaaagccat cttcgccatg ggcgtgctgg gctgccgcga catggaatac    600
ctctggggca atctggttaa attatccgat gctaatggct gcttcgccgc tggcgactct    660
gcctgtggct ttgccaacac cgccatggtt ctggccgaaa aaggctttat ccccatgtg     720 ttcgcagcgg ttatgcgtgt tgtggcagtg ccagagagcc tggtggcctt tgaacagggc    780
gcggttggcc cgagcaagga ctgcgcctat gaaggcccat acctcaaggc cattaccggc    840
agtcccatcg ccatggaagg taagagcgcg gctggcgccc atttaagccc agttggcaac    900
atcgcggcag ccgtggccga tacctggagt aatgaatcca tccagcaggt caagctctta    960
tccgagatgg cccctgtggt gggcatggaa cagctggtat atgactgccg tctcatgaac   1020
gtggccaagg aaaaaggcca gggccttatg atgcgcgacc tgctcgttga atctgacgcg   1080
ccgctggatg tccaggcatg ggttttaaga cccgatgttg tgcttaagat cgccggcgag   1140
ctggtgaaag agcaggataa cttcctgaga accaaactgg ccgccaaatt aaccattaac   1200
gagctgcgcg acgccatcaa ggccgaaaag gttaaggctg accgccgcga catgaaatgg   1260
ctcgacaaga tggaaaaagc agtggacaag attccagacg atccggaaca gttctacgca   1320
gaaatcaagc ccgagctgga catggacaag tggcatccta aaggctatgg cttaaaggcc   1380
tga                                                                 1383

<210> SEQ ID NO 25
<211> LENGTH: 475
<212> TYPE: PRT
<213> ORGANISM: Thermacetogenium phaeum

<400> SEQUENCE: 25

Met Glu Tyr Lys Pro Val Lys Thr Phe Asp Glu Leu Ala Val Lys Ser
1               5                   10                  15

Leu Asp Asp Phe Val Tyr Gly Ile Ala Pro His Val Thr Ala Lys
                20                  25                  30

Asn Gly Met Val Ile Gly Gly Gly Thr Val Tyr Pro Glu Ile Asn Leu
            35                  40                  45

Thr Leu Pro Pro Met Asn Ile Asn Glu Ser Thr Met Pro Glu Val Arg
```

```
            50                  55                  60
Arg Gln Tyr Ala Glu Met Ile Glu Gly Ile Leu Lys Arg Ala Lys Ser
65                   70                  75                  80

Leu Tyr Ala Pro Gly Ile Val Glu Val Glu Leu Leu Pro Glu Thr
                85                  90                  95

Thr Met Thr Pro Gln Trp Gly Ile Glu Ile Asn Lys Ile Leu Arg Asp
                100                 105                 110

Lys Met Tyr Glu Tyr Glu Asn Lys Tyr Gly Leu Lys Ser Leu Leu Arg
            115                 120                 125

Cys Thr Pro Asn Asp Thr Arg Glu Ile Val Arg Pro Pro Leu Met Arg
130                 135                 140

Arg Gly Glu Leu Leu Glu Asn Met Phe Thr Thr Phe Glu Lys Cys Ala
145                 150                 155                 160

Glu Asp Gly Ala Asp Ile Leu Ser Ile Glu Ser Thr Gly Gly Lys Glu
                165                 170                 175

Val His Asp Glu Gly Leu Val Thr Cys Asp Ile Arg Lys Val Val Phe
            180                 185                 190

Ala Leu Gly Val Leu Gly Val Arg Asp Met Arg Phe Leu Trp Ser Arg
        195                 200                 205

Ile Val Glu Ile Ala Gly Arg Thr Gly Ser Ile Ala Gly Gly Asp Thr
        210                 215                 220

Ala Cys Gly Phe Ala Asn Thr Ala Leu Ala Leu Ala Glu Gln Glu Met
225                 230                 235                 240

Ile Pro Arg Val Phe Ala Ala Val Asp Arg Val Ala Thr Ile Pro Arg
                245                 250                 255

Ser Leu Val Ala Phe Glu Met Gly Ala Thr Gly Pro Asp Lys Asp Cys
                260                 265                 270

Gly Tyr Glu Gly Pro Tyr Met Lys Ala Ile Ala Gly Val Pro Ile Ser
            275                 280                 285

Met Glu Gly Lys Thr Ala Ala Cys Ala His Leu Ser Ala Val Gly Asn
        290                 295                 300

Ile Ala Ala Cys Val Cys Asp Met Trp Ser Asn Glu Ser Val Gln Asn
305                 310                 315                 320

Val Lys Leu Leu Ser Ala Pro Ala Pro Val Val Ser Thr Glu Gln Leu
                325                 330                 335

Ile Tyr Asp Cys Arg Leu Met Asn Glu Ala Ala Asp Gly Arg Glu
            340                 345                 350

Phe Ala Leu Lys Met Arg Asp Trp Leu Ala Asp Ser Asp Ser Ser Leu
            355                 360                 365

Asp Pro Gln Ala Tyr Val Leu Arg Pro Asp Val Val Leu Glu Ile Ser
370                 375                 380

Gly Glu Leu Val Lys Glu Lys Asp Pro Phe Leu Ala Thr Lys Lys Ala
385                 390                 395                 400

Ala Ala Leu Ala Val Glu Val Ile Lys Arg Gly Val Glu Lys Gly Glu
                405                 410                 415

Leu Asn Leu Ser Ala Arg Glu Lys Lys Trp Leu Asp Ile Ile Ser Ser
                420                 425                 430

Gln Leu Glu Thr Ile Pro Asp Asp Glu Glu Lys Phe Trp Phe Glu Leu
            435                 440                 445

Gln Lys Glu Leu Asp Leu Asn Lys Trp Arg Pro Glu Glu Tyr Asp Leu
        450                 455                 460

Glu Val Ala Ala Ala Lys Ala Ala Ser Ala Lys
465                 470                 475
```

<210> SEQ ID NO 26
<211> LENGTH: 1428
<212> TYPE: DNA
<213> ORGANISM: Thermacetogenium phaeum

<400> SEQUENCE: 26

```
atggaataca agcctgtgaa aacctttgac gagctggctg tgaagtccct tgacgacttc        60
gtctacggga tagctcccca tcccgtaacg gcaaagaacg gcatggtgat cggcggggt       120 acggtctatc cggagatcaa cctgaccctc cccccatga atataaacga aagcaccatg       180
cccgaggtca gaaggcagta tgcggagatg atcgagggga ttctcaagag ggcgaagagc       240
ctctacgctc ccgggatcat cgtggaagtg gagctcttac ccgaaaccac catgaccccg       300
cagtggggga tcgagatcaa caagatcctg cgggacaaga tgtacgaata tgagaacaag       360
tacgggttga agagcctcct caggtgcacc cctaacgaca ccagagagat cgtcaggccg       420
ccgctgatga aaggggtga gctgctggag aacatgttca ccaccttcga gaagtgcgcc       480
gaagacggtg ccgacatcct ctccatcgag tccaccgggg gcaaagaggt tcacgacgaa       540
gggctcgtca cctgcgacat cagaaaggtc gtcttcgccc tgggcgtgct gggcgtcagg       600
gacatgcggt tcctctggtc gcgaatagtg gagatcgccg ggcggaccgg ctccatagcc       660
ggcggcgaca cggcgtgcgg cttcgccaac accgccctgg ccctggcgga gcaggagatg       720
atccccaggg tgttcgctgc ggtagaccgg gtggccacca tacccaggag cctggtggcg       780
ttcgaaatgg gtgccaccgg ccccgacaag gactgcggct atgaagggcc gtacatgaag       840
gccattgcag gagtgcccat ttccatggaa ggaaaaaccg cggcctgcgc ccacctgagc       900
gccgtcggca acattgccgc ctgcgtctgc gacatgtgga gcaacgaatc cgtccagaac       960
gtcaagctct taagcgctcc ggcccccgtg gtatccacgg agcagctcat ttacgactgc      1020
cggttgatga cgaagcggc agcggacgga cgggaattcg ccctgaagat gcgggactgg      1080
ctggccgact ccgactccag cctggatccc caggcctacg ttctgaggcc ggacgtagta      1140
ctggagatca gcggagagct ggtcaaggaa aagaccccct tcctggcgac caagaaggcg      1200
gccgccctgg cggtggaggt catcaagaga ggggtagaga aaggcgaact caatctctcg      1260
gccagagaaa agaagtggct ggacatcatc agctcccagc tcgaaaccat ccccgacgac      1320
gaggagaagt tctggttcga actgcagaaa gagctggatc tcaacaagtg gaggccggag      1380
gaatacgatt tagaggtggc cgcggccaaa gcggcatccg cgaaatag               1428
```